(12) United States Patent
Boncyk et al.

(10) Patent No.: US 8,938,096 B2
(45) Date of Patent: *Jan. 20, 2015

(54) IMAGE CAPTURE AND IDENTIFICATION SYSTEM AND PROCESS

(71) Applicant: Nant Holdings IP, LLC, Culver City, CA (US)

(72) Inventors: Wayne C. Boncyk, Evergreen, CO (US); Ronald H. Cohen, Pasadena, CA (US)

(73) Assignee: Nant Holdings IP, LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/907,819

(22) Filed: May 31, 2013

(65) Prior Publication Data

US 2013/0265435 A1    Oct. 10, 2013

Related U.S. Application Data

(60) Division of application No. 13/693,983, filed on Dec. 4, 2012, now Pat. No. 8,712,193, which is a continuation of application No. 13/069,112, filed on Mar. 22, 2011, now Pat. No. 8,326,031, which is a (Continued)

(51) Int. Cl.
  *G06K 9/00* (2006.01)
  *G06Q 20/24* (2012.01)

(Continued)

(52) U.S. Cl.
  CPC .......... *G06Q 20/24* (2013.01); *G06F 17/30259* (2013.01); *G06K 9/228* (2013.01); *G06K 9/4652* (2013.01); *G06K 9/4671* (2013.01); *G06K 9/6203* (2013.01); *G06Q 30/0277* (2013.01); *G06Q 30/0623* (2013.01); *G06Q 30/0643* (2013.01); *G06Q 40/00* (2013.01); *G06K 9/78* (2013.01); *G06Q 30/0601* (2013.01); *G06K 9/0063* (2013.01); *H04N 5/225* (2013.01); *G06Q 20/40145* (2013.01); *G06Q 30/0257* (2013.01);

(Continued)

(58) Field of Classification Search
  USPC ......... 382/103, 181, 100, 305; 705/26.1–27.2
  See application file for complete search history.

(56) References Cited

U.S. PATENT DOCUMENTS

| 4,947,321 A | 8/1990 | Spence et al. |
| 4,991,008 A | 2/1991 | Nama |

(Continued)

FOREIGN PATENT DOCUMENTS

| DE | 10050486 | 4/2002 |
| EP | 0614559 | 1/1999 |

(Continued)

OTHER PUBLICATIONS

Carswell J.D., et al., "An Environment for Mobile Context-Based Hypermedia Retrieval," IEEE: Proceedings of the 13th International Workshop on Database and Expert Systems Applications, 1529-4188/02, 2002, 5 pages.

(Continued)

*Primary Examiner* — Ishrat I Sherali
(74) *Attorney, Agent, or Firm* — Fish & Tsang, LLP

(57) ABSTRACT

A digital image of the object is captured and the object is recognized from plurality of objects in a database. An information address corresponding to the object is then used to access information and initiate communication pertinent to the object.

54 Claims, 7 Drawing Sheets

Related U.S. Application Data division of application No. 13/037,317, filed on Feb. 28, 2011, now Pat. No. 8,224,078, which is a division of application No. 12/333,630, filed on Dec. 12, 2008, now Pat. No. 7,899,243, which is a division of application No. 10/492,243, filed as application No. PCT/US02/35407 on Nov. 5, 2002, now Pat. No. 7,477,780, which is a continuation of application No. 09/992,942, filed on Nov. 5, 2001, now Pat. No. 7,016,532.

(60) Provisional application No. 60/317,521, filed on Sep. 5, 2001, provisional application No. 60/246,295, filed on Nov. 6, 2000.

(51) Int. Cl.

| | | |
|---|---|---|
| *G06F 17/30* | (2006.01) | |
| *G06K 9/22* | (2006.01) | |
| *G06K 9/46* | (2006.01) | |
| *G06K 9/62* | (2006.01) | |
| *G06Q 30/02* | (2012.01) | |
| *G06Q 30/06* | (2012.01) | |
| *G06Q 40/00* | (2012.01) | |
| *G06K 9/78* | (2006.01) | |
| *H04N 5/225* | (2006.01) | |
| *G06Q 20/40* | (2012.01) | |
| *A61F 9/08* | (2006.01) | |
| *H04N 7/18* | (2006.01) | |
| *A63F 13/00* | (2014.01) | |
| *H04N 21/81* | (2011.01) | |
| *G06K 9/32* | (2006.01) | |
| *A63F 13/30* | (2014.01) | |
| *H04N 21/254* | (2011.01) | |
| *H04N 21/442* | (2011.01) | |
| *G06Q 10/02* | (2012.01) | |
| *H04N 5/232* | (2006.01) | |
| *G06Q 20/34* | (2012.01) | |

(52) U.S. Cl.
CPC *A61F 9/08* (2013.01); *H04N 7/183* (2013.01); *A63F 13/00* (2013.01); *H04N 21/8173* (2013.01); *G06K 9/3241* (2013.01); *G06F 17/30386* (2013.01); *A63F 13/12* (2013.01); *G06K 9/6201* (2013.01); *G06Q 30/0267* (2013.01); *G06Q 30/0268* (2013.01); *G06Q 30/0269* (2013.01); *H04N 21/254* (2013.01); *H04N 21/44222* (2013.01); *H04N 21/8126* (2013.01); *G06Q 30/0253* (2013.01); *H04N 21/812* (2013.01); *G06K 9/00536* (2013.01); *G06K 9/6202* (2013.01); *G06Q 10/02* (2013.01); *H04N 5/23222* (2013.01); *G06F 17/30256* (2013.01); *G06F 17/30247* (2013.01); *G06Q 20/3567* (2013.01); *G06Q 30/0217* (2013.01)
USPC .................................................... 382/103

(56) References Cited

U.S. PATENT DOCUMENTS

| | | |
|---|---|---|
| 5,034,812 A | 7/1991 | Rawlings |
| 5,241,671 A | 8/1993 | Reed et al. |
| 5,259,037 A | 11/1993 | Plunk |
| 5,497,314 A | 3/1996 | Novak |
| 5,576,950 A | 11/1996 | Tonomura et al. |
| 5,579,471 A | 11/1996 | Barber et al. |
| 5,594,806 A | 1/1997 | Colbert |
| 5,615,324 A | 3/1997 | Kuboyama |
| 5,625,765 A | 4/1997 | Ellenby et al. |
| 5,682,332 A | 10/1997 | Ellenby et al. |
| 5,724,579 A | 3/1998 | Suzuki |
| 5,742,521 A | 4/1998 | Ellenby et al. |
| 5,742,815 A | 4/1998 | Stern |
| 5,751,286 A | 5/1998 | Barber et al. |
| 5,768,633 A | 6/1998 | Allen et al. |
| 5,768,663 A | 6/1998 | Lin |
| 5,771,307 A | 6/1998 | Lu et al. |
| 5,815,411 A | 9/1998 | Ellenby et al. |
| 5,893,095 A | 4/1999 | Jain et al. |
| 5,894,323 A | 4/1999 | Kain et al. |
| 5,897,625 A | 4/1999 | Gustin et al. |
| 5,911,827 A | 6/1999 | Heller |
| 5,915,038 A | 6/1999 | Abdel-Mottaleb et al. |
| 5,917,930 A | 6/1999 | Kayani et al. |
| 5,926,116 A | 7/1999 | Kitano et al. |
| 5,933,823 A | 8/1999 | Cullen et al. |
| 5,933,829 A | 8/1999 | Durst et al. |
| 5,933,923 A | 8/1999 | Catlos et al. |
| 5,945,982 A | 8/1999 | Higashio et al. |
| 5,971,277 A | 10/1999 | Cragun et al. |
| 5,978,773 A | 11/1999 | Hudetz et al. |
| 5,982,912 A | 11/1999 | Fukui et al. |
| 5,991,827 A | 11/1999 | Ellenby et al. |
| 5,992,752 A | 11/1999 | Wilz, Sr. et al. |
| 6,009,204 A | 12/1999 | Ahmad |
| 6,031,545 A | 2/2000 | Ellenby et al. |
| 6,037,936 A | 3/2000 | Ellenby et al. |
| 6,037,963 A | 3/2000 | Denton et al. |
| 6,038,333 A | 3/2000 | Wang |
| 6,045,039 A | 4/2000 | Stinson et al. |
| 6,055,536 A | 4/2000 | Shimakawa et al. |
| 6,061,478 A | 5/2000 | Kanoh et al. |
| 6,064,398 A | 5/2000 | Ellenby et al. |
| 6,072,904 A | 6/2000 | Desai et al. |
| 6,081,612 A | 6/2000 | Gutkowicz-Krusin et al. |
| 6,098,118 A | 8/2000 | Ellenby et al. |
| 6,108,656 A | 8/2000 | Durst et al. |
| 6,134,548 A | 10/2000 | Gottsman et al. |
| 6,144,848 A | 11/2000 | Walsh et al. |
| 6,173,239 B1 | 1/2001 | Ellenby |
| 6,181,817 B1 | 1/2001 | Zabih et al. |
| 6,182,090 B1 | 1/2001 | Peairs |
| 6,199,048 B1 | 3/2001 | Hudetz et al. |
| 6,202,055 B1 | 3/2001 | Houvener et al. |
| 6,208,353 B1 | 3/2001 | Ayer et al. |
| 6,208,749 B1 | 3/2001 | Gutkowicz-Krusin et al. |
| 6,208,933 B1 | 3/2001 | Lazar |
| 6,256,409 B1 | 7/2001 | Wang |
| 6,278,461 B1 | 8/2001 | Ellenby et al. |
| 6,286,036 B1 | 9/2001 | Rhoads |
| 6,307,556 B1 | 10/2001 | Ellenby et al. |
| 6,307,957 B1 | 10/2001 | Gutkowicz-Krusin et al. |
| 6,317,718 B1 | 11/2001 | Fano |
| 6,393,147 B2 | 5/2002 | Danneels et al. |
| 6,396,475 B1 | 5/2002 | Ellenby et al. |
| 6,396,537 B1 | 5/2002 | Squilla et al. |
| 6,396,963 B2 | 5/2002 | Shaffer et al. |
| 6,404,975 B1 | 6/2002 | Bopardikar et al. |
| 6,405,975 B1 | 6/2002 | Sankrithi et al. |
| 6,411,725 B1 | 6/2002 | Rhoads |
| 6,414,696 B1 | 7/2002 | Ellenby et al. |
| 6,430,554 B1 | 8/2002 | Rothschild |
| 6,434,561 B1 | 8/2002 | Durst, Jr. et al. |
| 6,446,076 B1 | 9/2002 | Burkey et al. |
| 6,453,361 B1 | 9/2002 | Morris |
| 6,490,443 B1 | 12/2002 | Freeny, Jr. |
| 6,501,854 B1 | 12/2002 | Konishi et al. |
| 6,502,756 B1 | 1/2003 | Fahraeus |
| 6,510,238 B2 | 1/2003 | Haycock |
| 6,522,292 B1 | 2/2003 | Ellenby et al. |
| 6,522,772 B1 | 2/2003 | Morrison et al. |
| 6,522,889 B1 | 2/2003 | Aarnio |
| 6,526,158 B1 | 2/2003 | Boldberg |
| 6,532,298 B1 | 3/2003 | Cambier et al. |
| 6,533,392 B1 | 3/2003 | Koitabashi |
| 6,535,210 B1 | 3/2003 | Ellenby et al. |
| 6,542,933 B1 | 4/2003 | Durst, Jr. et al. |
| 6,563,959 B1 | 5/2003 | Troyanker |
| 6,567,122 B1 | 5/2003 | Anderson et al. |

(56) References Cited

U.S. PATENT DOCUMENTS

| | | |
|---|---|---|
| 6,578,017 B1 | 6/2003 | Ebersole et al. |
| 6,597,818 B2 | 7/2003 | Kumarr et al. |
| 6,601,026 B2 | 7/2003 | Appelt et al. |
| 6,609,103 B1 | 8/2003 | Kolls |
| 6,650,794 B1 | 11/2003 | Aoki |
| 6,651,053 B1 | 11/2003 | Rothschild |
| 6,658,389 B1 | 12/2003 | Alpdemir |
| 6,674,923 B1 | 1/2004 | Shih et al. |
| 6,674,993 B1 | 1/2004 | Tarbouriech |
| 6,675,165 B1 | 1/2004 | Rothschild |
| 6,689,966 B2 | 2/2004 | Wiebe |
| 6,690,370 B2 | 2/2004 | Ellenby et al. |
| 6,691,914 B2 | 2/2004 | Isherwood et al. |
| 6,711,278 B1 | 3/2004 | Gu et al. |
| 6,714,969 B1 | 3/2004 | Klein et al. |
| 6,724,914 B2 | 4/2004 | Brundage et al. |
| 6,738,630 B2 | 5/2004 | Ashmore |
| 6,744,935 B2 | 6/2004 | Choi et al. |
| 6,748,122 B1 | 6/2004 | Ihara et al. |
| 6,765,569 B2 | 7/2004 | Neumann et al. |
| 6,766,363 B1 | 7/2004 | Rothschild |
| 6,771,294 B1 | 8/2004 | Pulli et al. |
| 6,801,657 B1 | 10/2004 | Cieplinski |
| 6,804,726 B1 | 10/2004 | Ellenby et al. |
| 6,842,181 B2 | 1/2005 | Acharya |
| 6,853,750 B2 | 2/2005 | Aoki |
| 6,856,965 B1 | 2/2005 | Stinson et al. |
| 6,865,608 B2 | 3/2005 | Hunter |
| 6,866,196 B1 | 3/2005 | Rathus et al. |
| 6,868,415 B2 | 3/2005 | Kageyama et al. |
| 6,882,756 B1 | 4/2005 | Bober |
| 6,885,771 B2 | 4/2005 | Takahashi |
| 6,912,464 B1 | 6/2005 | Parker |
| 6,925,196 B2 | 8/2005 | Kass et al. |
| 6,950,800 B1 | 9/2005 | McIntyre et al. |
| 6,956,593 B1 | 10/2005 | Gupta et al. |
| 6,968,453 B2 | 11/2005 | Doyle et al. |
| 6,974,078 B1 | 12/2005 | Simon |
| 6,985,240 B2 | 1/2006 | Benke et al. |
| 6,993,573 B2 | 1/2006 | Hunter |
| 6,996,251 B2 | 2/2006 | Malone et al. |
| 7,002,551 B2 | 2/2006 | Azuma et al. |
| 7,016,532 B2* | 3/2006 | Boncyk et al. ................. 382/165 |
| 7,016,889 B2 | 3/2006 | Bazoon |
| 7,016,899 B1 | 3/2006 | Stern et al. |
| 7,027,652 B1 | 4/2006 | I'Anson |
| 7,031,496 B2 | 4/2006 | Shimano et al. |
| 7,031,536 B2 | 4/2006 | Kajiwara |
| 7,031,875 B2 | 4/2006 | Ellenby et al. |
| 7,050,653 B2 | 5/2006 | Edso et al. |
| 7,053,916 B2 | 5/2006 | Kobayashi et al. |
| 7,062,454 B1 | 6/2006 | Giannini et al. |
| 7,103,772 B2 | 9/2006 | Jorgensen et al. |
| 7,119,831 B2 | 10/2006 | Ohto et al. |
| 7,127,094 B1 | 10/2006 | Elbaum et al. |
| 7,143,949 B1 | 12/2006 | Hannigan |
| 7,167,164 B2 | 1/2007 | Ericson et al. |
| 7,175,095 B2 | 2/2007 | Petterson et al. |
| 7,224,995 B2 | 5/2007 | Rhoads |
| 7,245,273 B2 | 7/2007 | Eberl et al. |
| 7,254,548 B1 | 8/2007 | Tannenbaum |
| 7,295,718 B2 | 11/2007 | Park et al. |
| 7,301,536 B2 | 11/2007 | Ellenby et al. |
| 7,305,354 B2 | 12/2007 | Rodriguez et al. |
| 7,309,015 B2 | 12/2007 | Frantz et al. |
| 7,310,605 B2* | 12/2007 | Janakiraman et al. ........ 704/277 |
| 7,333,947 B2 | 2/2008 | Wiebe et al. |
| 7,345,673 B2 | 3/2008 | Ericson et al. |
| 7,353,182 B1 | 4/2008 | Missinhoun et al. |
| 7,353,184 B2 | 4/2008 | Kirshenbaum et al. |
| 7,353,990 B2 | 4/2008 | Elliot et al. |
| 7,356,705 B2 | 4/2008 | Ting |
| 7,362,922 B2 | 4/2008 | Nishiyama et al. |
| 7,376,645 B2 | 5/2008 | Bernard |
| 7,383,209 B2 | 6/2008 | Hudetz et al. |
| 7,410,099 B2 | 8/2008 | Fukasawa et al. |
| 7,427,980 B1 | 9/2008 | Partridge et al. |
| 7,430,588 B2 | 9/2008 | Hunter |
| 7,477,909 B2 | 1/2009 | Roth et al. |
| 7,526,440 B2 | 4/2009 | Walker et al. |
| 7,548,915 B2 | 6/2009 | Ramer et al. |
| 7,558,595 B2 | 7/2009 | Angelhag |
| 7,564,469 B2 | 7/2009 | Cohen |
| 7,580,061 B2 | 8/2009 | Toyoda |
| 7,595,816 B1 | 9/2009 | Enright et al. |
| 7,641,342 B2 | 1/2010 | Eberl et al. |
| 7,680,324 B2 | 3/2010 | Boncyk et al. |
| 7,696,905 B2 | 4/2010 | Ellenby et al. |
| 7,711,598 B2 | 5/2010 | Perkowski |
| 7,720,436 B2 | 5/2010 | Hamynen et al. |
| 7,734,507 B2 | 6/2010 | Ritter |
| 7,737,965 B2 | 6/2010 | Alter et al. |
| 7,756,755 B2 | 7/2010 | Ghosh et al. |
| 7,764,808 B2 | 7/2010 | Zhu et al. |
| 7,765,126 B2 | 7/2010 | Hudetz et al. |
| 7,768,534 B2 | 8/2010 | Pentenrieder et al. |
| 7,769,228 B2 | 8/2010 | Bahlmann et al. |
| 7,774,283 B2 | 8/2010 | Das et al. |
| 7,775,437 B2 | 8/2010 | Cohen |
| 7,830,417 B2 | 11/2010 | Liu et al. |
| 7,845,558 B2 | 12/2010 | Beemer et al. |
| 7,872,669 B2 | 1/2011 | Darrell et al. |
| 7,889,193 B2 | 2/2011 | Platonov et al. |
| 7,896,235 B2 | 3/2011 | Ramachandran |
| 7,916,138 B2 | 3/2011 | John et al. |
| 8,090,616 B2 | 1/2012 | Proctor, Jr. et al. |
| 8,099,332 B2 | 1/2012 | Lemay et al. |
| 8,121,944 B2 | 2/2012 | Norman et al. |
| 8,130,242 B2 | 3/2012 | Cohen |
| 8,131,118 B1 | 3/2012 | Jing et al. |
| 8,131,595 B2 | 3/2012 | Lee et al. |
| 8,189,964 B2 | 5/2012 | Flynn et al. |
| 8,218,874 B2 | 7/2012 | Boncyk et al. |
| 8,219,146 B2 | 7/2012 | Connors et al. |
| 8,255,291 B1 | 8/2012 | Nair |
| 8,312,168 B2 | 11/2012 | Rhoads et al. |
| 8,320,615 B2 | 11/2012 | Hamza et al. |
| 8,326,031 B2 | 12/2012 | Boncyk et al. |
| 8,335,351 B2 | 12/2012 | Boncyk et al. |
| 8,386,918 B2* | 2/2013 | Do et al. ................. 715/230 |
| 8,442,500 B2* | 5/2013 | Gupta et al. ................. 455/414.1 |
| 8,447,066 B2 | 5/2013 | King et al. |
| 8,494,274 B2 | 7/2013 | Badharudeen et al. |
| 8,542,906 B1* | 9/2013 | Persson et al. ................. 382/154 |
| 8,588,527 B2 | 11/2013 | Boncyk et al. |
| 8,605,141 B2* | 12/2013 | Dialameh et al. ............. 348/62 |
| 8,626,602 B2 | 1/2014 | George |
| 2001/0011276 A1 | 8/2001 | Durst, Jr. et al. |
| 2001/0032252 A1 | 10/2001 | Durst, Jr. et al. |
| 2001/0044824 A1 | 11/2001 | Hunter et al. |
| 2001/0047426 A1 | 11/2001 | Hunter |
| 2001/0053252 A1 | 12/2001 | Creque |
| 2002/0001398 A1 | 1/2002 | Shimano et al. |
| 2002/0006602 A1 | 1/2002 | Masters |
| 2002/0019819 A1 | 2/2002 | Sekiguchi et al. |
| 2002/0048403 A1 | 4/2002 | Guerreri |
| 2002/0055957 A1 | 5/2002 | Ohsawa |
| 2002/0084328 A1 | 7/2002 | Kim |
| 2002/0089524 A1 | 7/2002 | Ikeda |
| 2002/0090132 A1 | 7/2002 | Boncyk et al. |
| 2002/0102966 A1 | 8/2002 | Lev et al. |
| 2002/0103813 A1 | 8/2002 | Frigon |
| 2002/0124188 A1 | 9/2002 | Sherman et al. |
| 2002/0140988 A1 | 10/2002 | Cheatle et al. |
| 2002/0150298 A1 | 10/2002 | Rajagopal et al. |
| 2002/0156866 A1 | 10/2002 | Schneider |
| 2002/0163521 A1 | 11/2002 | Ellenby et al. |
| 2002/0167536 A1 | 11/2002 | Valdes et al. |
| 2003/0064705 A1 | 4/2003 | Desiderio |
| 2003/0095681 A1 | 5/2003 | Burg et al. |
| 2003/0116478 A1 | 6/2003 | Laskowski |
| 2003/0164819 A1 | 9/2003 | Waibel |
| 2004/0208372 A1 | 10/2004 | Boncyk et al. |
| 2005/0015370 A1 | 1/2005 | Stavely et al. |

(56) References Cited

U.S. PATENT DOCUMENTS

| | | |
|---|---|---|
| 2005/0024501 A1 | 2/2005 | Ellenby et al. |
| 2005/0102233 A1 | 5/2005 | Park et al. |
| 2005/0162523 A1 | 7/2005 | Darrell et al. |
| 2005/0162532 A1 | 7/2005 | Toyoda |
| 2005/0185060 A1 | 8/2005 | Neven et al. |
| 2005/0206654 A1 | 9/2005 | Vaha-Sipila |
| 2005/0252966 A1 | 11/2005 | Kulas |
| 2006/0008124 A1 | 1/2006 | Ewe et al. |
| 2006/0038833 A1 | 2/2006 | Mallinson et al. |
| 2006/0161379 A1 | 7/2006 | Ellenby et al. |
| 2006/0190812 A1 | 8/2006 | Ellenby et al. |
| 2006/0223635 A1 | 10/2006 | Rosenberg |
| 2007/0109619 A1 | 5/2007 | Eberl et al. |
| 2007/0146391 A1 | 6/2007 | Pentenrieder et al. |
| 2007/0182739 A1 | 8/2007 | Platonov et al. |
| 2008/0021953 A1 | 1/2008 | Gil |
| 2008/0157946 A1 | 7/2008 | Eberl et al. |
| 2008/0243721 A1 | 10/2008 | Joao |
| 2008/0279481 A1 | 11/2008 | Ando |
| 2009/0027337 A1 | 1/2009 | Hildreth |
| 2010/0045933 A1 | 2/2010 | Eberl et al. |
| 2010/0188638 A1 | 7/2010 | Eberl et al. |
| 2011/0173100 A1 | 7/2011 | Boncyk et al. |
| 2012/0002872 A1 | 1/2012 | Boncyk et al. |
| 2012/0011119 A1 | 1/2012 | Baheti et al. |
| 2012/0011142 A1 | 1/2012 | Baheti et al. |
| 2012/0072353 A1 | 3/2012 | Boone et al. |
| 2012/0095857 A1 | 4/2012 | McKelvey et al. |
| 2012/0231887 A1 | 9/2012 | Lee et al. |

FOREIGN PATENT DOCUMENTS

| | | |
|---|---|---|
| EP | 0920179 A2 | 6/1999 |
| EP | 0967574 A2 | 12/1999 |
| EP | 1012725 A1 | 6/2000 |
| EP | 0920179 A3 | 9/2000 |
| EP | 1354260 A2 | 10/2003 |
| EP | 1355258 A2 | 10/2003 |
| EP | 2264669 A2 | 12/2010 |
| GB | 2407230 A | 4/2005 |
| JP | S6314297 A | 1/1988 |
| JP | H09231244 A | 9/1997 |
| JP | H1091634 A | 4/1998 |
| JP | H10289243 A | 10/1998 |
| JP | H11265391 A | 9/1999 |
| JP | 2001101191 A | 4/2001 |
| JP | 2001160057 A | 6/2001 |
| JP | 2001256500 A | 9/2001 |
| JP | 2001265970 A | 9/2001 |
| JP | 2001282825 A | 10/2001 |
| JP | 2002197103 A | 7/2002 |
| JP | 2002297648 A | 10/2002 |
| JP | 2003178067 A | 6/2003 |
| JP | 2003323440 A | 11/2003 |
| JP | 2004005314 A | 1/2004 |
| JP | 2004030377 A | 1/2004 |
| JP | 2004118384 A | 4/2004 |
| JP | 2005011180 A | 1/2005 |
| JP | 2005038421 A | 2/2005 |
| JP | 2005049920 A | 2/2005 |
| JP | 2005509219 A | 4/2005 |
| JP | 2007509392 A | 4/2007 |
| WO | 9744737 A1 | 11/1997 |
| WO | 9749060 A1 | 12/1997 |
| WO | 9837811 A1 | 9/1998 |
| WO | WO9846323 | 10/1998 |
| WO | 9916024 A1 | 4/1999 |
| WO | 9942946 A2 | 8/1999 |
| WO | 9942947 A2 | 8/1999 |
| WO | 9944010 A1 | 9/1999 |
| WO | 9942946 A3 | 10/1999 |
| WO | 9942947 A3 | 12/1999 |
| WO | 9967695 A2 | 12/1999 |
| WO | 0124050 A1 | 4/2001 |
| WO | 0149056 A1 | 7/2001 |
| WO | 0163487 A1 | 8/2001 |
| WO | 0171282 A1 | 9/2001 |
| WO | 0173603 A1 | 10/2001 |
| WO | 0201143 A2 | 1/2002 |
| WO | 02059716 A2 | 8/2002 |
| WO | 02073818 A1 | 9/2002 |
| WO | 02082799 A2 | 10/2002 |
| WO | 03041000 A1 | 5/2003 |

OTHER PUBLICATIONS

Chang S.F., et al., "Visual Information Retrieval from Large Distributed Online Respositories," Communication of Association for Computing Machinery, ISSN:0001-0782, 1997, vol. 40 (12), pp. 64-71.

Supplementary European Search Report for Application No. EP02778730, mailed on May 14, 2007, 3 pages.

Supplementary European Search Report for Application No. EP06801326, mailed on Aug. 12, 2008, 8 pages.

Yeh T., et al., "Searching the Web with Mobile Images for location Recognition," IEEE: Proceedings of the 2004 IEEE Computer Society Conference on Computer Vision and Pattern Recognition (CVPR'04), 1063-6919/04, 2004, 6 pages.

European Search Report for Application No. EP06018047, mailed on Oct. 30, 2008, 2 pages.

International Search Report and Written Opinion for Application No. PCT/US2007/02010, mailed on Nov. 16, 2007, 5 pages.

Levine, Jeffrey M; Real-Time Target and Pose Recognition for 3-D Graphical Overlay; Massachusetts Institute of Technology, Jun. 1997.

Yang, Jie et al; Smart Sight: A Tourist Assistant System; Interactive Systems Laboratories, Carnegie Melon University.

Zhang, Xiang et al; Taking AR into Large Scale Industrial Environments: Navigation and Information Access with Mobile Computers.

Wagner, Daniel et al; First Steps Towards Handheld Augmented Reality; Vienna University of Technology; Favoritensrt. 9-11/118/2; A1040 Vienna, Austria.

Toye, Eleanor et al; Interacting with Mobile Services; An Evaluation of Camera-Phones and Visual Tags; Springer-Verlag, London Limited 2006.

Suzuki, Genta et al; u-Photo: Interacting with Pervasive Services using Digital Still Images; Graduate School of Media and Governance, Keio University; Japan.

Starner, Jennifer et al; Augmented Reality Through Wearable Computing; Massachusetts Institute of Technology.

Smith, John R. et al; Visual SEEk: a Fully Automated Content-Based Image Query System; Center for Image Technology for New Media, Columbia University, New York, New York.

Smailagic, Asim et al; Metronaut: A Wearable Computer with Sensing and Global Communication Capabilities; Carnegie Mellon University; Pittsburg, PA.

Siltanen, Sanni et al; Implementing a Natural User Interface for Camera Phones Using Visual Rags; VTT Information Technology.

Rohs, Michael et al; A Conceptual Framework for Camera Phone-based Interaction Techniques; Institute for Pervasive Computing, Department of Computer Science, Swiss Federal Institute of Technology; Zurich, CH.

Rekimoto, Jun; NaviCam: A Palmtop Device APproach to Augmented Reality; Sony Computer Science Laboratory , Inc.

Rekimoto, Jun et al; CyberCode: Designing Augmented Reality Environments with Visual Tags; Interaction Laboratory, Sony Computer Science Laboratory , Inc.; Tokyo, JP.

Rekimoto, Jun et al; Augmented-able Reality: Situated COmmunication through Physical and Digital Spaces; ony Computer Science Laboratory, Sony Corporation Informaiton Technology Laboratories and Department of Informaiton Science, Tokyo Institute of Technology; Tokyo, JP.

Rekimoto, Jun et al; The World Through the Computer: Computer Augmented Interactions with Real World Environments; Sony Computer Science Laboratory , Inc.; Tokyo, JP.

Ljungstrand, Peter et al; WebStickers: Using Physical Tokens to Acces, Manage and Share Bookmarks to the Web; Play: Applied research on art and technology; Interactive Institute c/o Viktoria Institute; Goteborg, SE.

(56) References Cited

OTHER PUBLICATIONS

Klinker, Gudrun et al; Augmented Maintenance of Powerplants: A Prototyping Case Study of a Mobile AR System; Tescnische Universitat Munchen; Munchen, DE.

Kato, Hirokazu et al; Marker Tracking and HMD Calibration for a Video-Based Augmented Reality Conferencing System; Faculty of Information Sciences, Hiroshima City University and Human Interface Technology Laboratory, University of Washington.

Kangas, Kari et al; Using Code Mobility to Create Ubiquitous and Active Augmented Reality in Mobile Computing; University of Oulu, Department of Electrical Engineering, Computer Engineering Laboratory; Oulu, Finland.

Jebara, Tony et al; Stochasticks: Augmenting the Billiards Experience with Probabilistic Vision and Wearable Conputers; Media Laboratory; Massachusetts Institute of Technology.

Iwaoka, Toshiyuki et al; Digital Safari Guidebook with Image Retrieval; OMRON Corporation, Information Technology Research Center; Kyoto, JP.

Iwamoto, Takeshi et al; u-Photo: A Design and Implementation of a Snapshot Based Method for Capturing Contextual Information; Graduate School of Medial Governance, Keio University.

Holler, Tobias H. et al; Mobile Augmented Reality; Chapter Nine; Telegeoinformatics: Location-Based Computing and Services; H. Karimi and A. Hammad (eds.); Taylor & Francis Books Ltd; Jan. 2004.

Haritaoglu, Ismail; InfoScope: Link from Real World Digital Information Space; IBM Almaden Research; San Jose, CA.

Gevers, Theo et al; PicToSeek: Combining Color and Shape Invariant Features for Image Retrieval; IEEE Transactions on Inage Processing, vol. 9, No. 1; Jan. 2000.

Geiger, Christian et al; Mobile AR4ALL; C-Lab; Paderborn, DE.

Fernandez, Francisco; Responsive Environments: Digital Objects in the Landscape; Department of Landscape Architecture; University of Manitoba; Winnipeg, Manitoba; Mar. 2004.

Feiner, Steven et al; A Touring Machine: Prototyping 3D Mobile Augmented Reality Systems for Exploring the Urban Environment; Department of Computer Science; Columbia University and Graduate School of Architecture, Planning and Preservation; Columbia University; Personal Technologies, 1(4), 1997, pp. 208-217.

Diverdi, Stephen et al; Level of Detail Interfaces; Department of Computer Science, University of California, Santa Barbara; IEEE/ACM Intl. Symp. on Mixed and Augmented Reality; Arlington, VA; Nov. 2-5, 2004.

Diverdi, Stephen et al; ARWin—A Desktop Augmented Reality Window Manager; Department of Computer Science, University of California, Santa Barbara; May 2003.

Arai; Toshifumi et al; PaperLink: A Technique for Hyperlinking from Real Paper to Electronic Content; CHI 97, Mar. 22-27, 1997.

Bulman, J. et al; Mixed Reality Applicaitons in Urban Environments; BT Technology Journal; vol. 22, No. 3; Jul. 2004.

Chang, Wendy et al; Efficient Resource Selection in Distributed Visual Information Systems; Department of Computer Science, State University of New York at Buffalo; Buffalo, NY.

\* cited by examiner

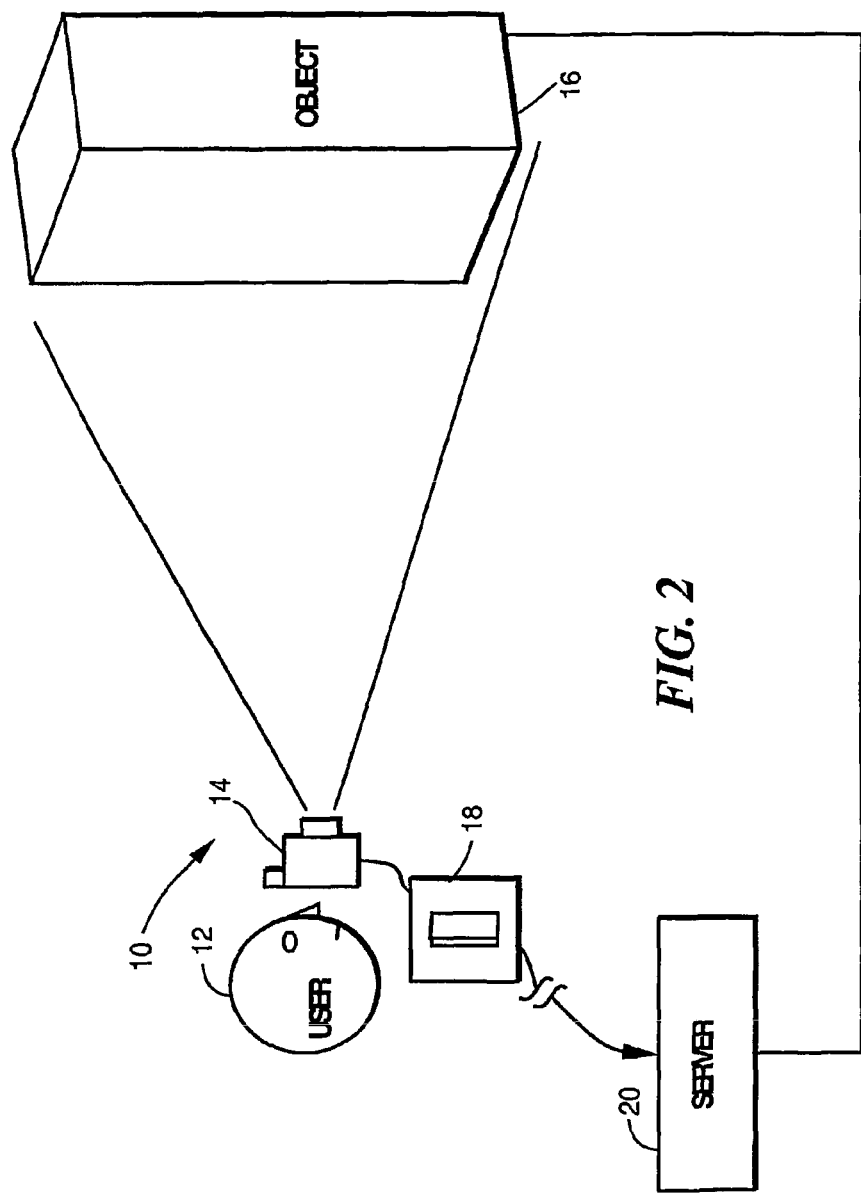

US 8,938,096 B2

IMAGE CAPTURE AND IDENTIFICATION SYSTEM AND PROCESS

This application is a divisional of Ser. No. 13/693,983, filed Dec. 4, 2012, which is a continuation of Ser. No. 13/069,112, filed Mar. 22, 2011 and issued Dec. 4, 2012 as U.S. Pat. No. 8,326,031, which is a divisional of Ser. No. 13/037,317 filed Feb. 28, 2011 and issued Jul. 17, 2012 as U.S. Pat. No. 8,224,078, which is a divisional of Ser. No. 12/333,630 filed Dec. 12, 2008 and issued Mar. 1, 2011 as U.S. Pat. No. 7,899,243, which is a divisional of Ser. No. 10/492,243 filed May 20, 2004 and issued Jan. 13, 2009 as U.S. Pat. No. 7,477,780, which is a National Phase of PCT/US02/35407 filed Nov. 5, 2002, which is an International Patent application and a continuation-in-part of Ser. No. 09/992,942 filed Nov. 5, 2001 and issued Mar. 21, 2006 as U.S. Pat. No. 7,016,532, which claims priority to provisional application No. 60/317,521 filed Sep. 5, 2001 and provisional application No. 60/246,295 filed Nov. 6, 2000. These and all other referenced patents and applications are incorporated herein by reference in their entirety. Where a definition or use of a term in a reference that is incorporated by reference is inconsistent or contrary to the definition of that term provided herein, the definition of that term provided herein is deemed to be controlling of that term provided herein, the definition of that term provided herein is deemed to be controlling.

TECHNICAL FIELD

The invention relates an identification method and process for objects from digitally captured images thereof that uses image characteristics to identify an object from a plurality of objects in a database.

BACKGROUND ART

There is a need to provide hyperlink functionality in known objects without modification to the objects, through reliably detecting and identifying the objects based only on the appearance of the object, and then locating and supplying information pertinent to the object or initiating communications pertinent to the object by supplying an information address, such as a Uniform Resource Locator (URL), pertinent to the object.

There is a need to determine the position and orientation of known objects based only on imagery of the objects.

The detection, identification, determination of position and orientation, and subsequent information provision and communication must occur without modification or disfigurement of the object, without the need for any marks, symbols, codes, barcodes, or characters on the object, without the need to touch or disturb the object, without the need for special lighting other than that required for normal human vision, without the need for any communication device (radio frequency, infrared, etc.) to be attached to or nearby the object, and without human assistance in the identification process. The objects to be detected and identified may be 3-dimensional objects, 2-dimensional images (e.g., on paper), or 2-dimensional images of 3-dimensional objects, or human beings.

There is a need to provide such identification and hyperlink services to persons using mobile computing devices, such as Personal Digital Assistants (PDAs) and cellular telephones.

There is a need to provide such identification and hyperlink services to machines, such as factory robots and spacecraft.

Examples include:

identifying pictures or other art in a museum, where it is desired to provide additional information about such art objects to museum visitors via mobile wireless devices;

provision of content (information, text, graphics, music, video, etc.), communications, and transaction mechanisms between companies and individuals, via networks (wireless or otherwise) initiated by the individuals "pointing and clicking" with camera-equipped mobile devices on magazine advertisements, posters, billboards, consumer products, music or video disks or tapes, buildings, vehicles, etc.;

establishment of a communications link with a machine, such a vending machine or information kiosk, by "pointing and clicking" on the machine with a camera-equipped mobile wireless device and then execution of communications or transactions between the mobile wireless device and the machine;

identification of objects or parts in a factory, such as on an assembly line, by capturing an image of the objects or parts, and then providing information pertinent to the identified objects or parts;

identification of a part of a machine, such as an aircraft part, by a technician "pointing and clicking" on the part with a camera-equipped mobile wireless device, and then supplying pertinent content to the technician, such maintenance instructions or history for the identified part;

identification or screening of individual(s) by a security officer "pointing and clicking" a camera-equipped mobile wireless device at the individual(s) and then receiving identification information pertinent to the individuals after the individuals have been identified by face recognition software;

identification, screening, or validation of documents, such as passports, by a security officer "pointing and clicking" a camera-equipped device at the document and receiving a response from a remote computer;

determination of the position and orientation of an object in space by a spacecraft nearby the object, based on imagery of the object, so that the spacecraft can maneuver relative to the object or execute a rendezvous with the object;

identification of objects from aircraft or spacecraft by capturing imagery of the objects and then identifying the objects via image recognition performed on a local or remote computer;

watching movie previews streamed to a camera-equipped wireless device by "pointing and clicking" with such a device on a movie theatre sign or poster, or on a digital video disc box or videotape box;

listening to audio recording samples streamed to a camera-equipped wireless device by "pointing and clicking" with such a device on a compact disk (CD) box, videotape box, or print media advertisement;

purchasing movie, concert, or sporting event tickets by "pointing and clicking" on a theater, advertisement, or other object with a camera-equipped wireless device;

purchasing an item by "pointing and clicking" on the object with a camera-equipped wireless device and thus initiating a transaction;

interacting with television programming by "pointing and clicking" at the television screen with a camera-equipped device, thus capturing an image of the screen content and having that image sent to a remote computer and identified, thus initiating interaction based on the screen content received (an example is purchasing an item on the television screen by "pointing and clicking" at the screen when the item is on the screen);

interacting with a computer-system based game and with other players of the game by "pointing and clicking" on objects in the physical environment that are considered to be part of the game;

paying a bus fare by "pointing and clicking" with a mobile wireless camera-equipped device, on a fare machine in a bus, and thus establishing a communications link between the device and the fare machine and enabling the fare payment transaction;

establishment of a communication between a mobile wireless camera-equipped device and a computer with an Internet connection by "pointing and clicking" with the device on the computer and thus providing to the mobile device an Internet address at which it can communicate with the computer, thus establishing communications with the computer despite the absence of a local network or any direct communication between the device and the computer;

use of a mobile wireless camera-equipped device as a point-of-sale terminal by, for example, "pointing and clicking" on an item to be purchased, thus identifying the item and initiating a transaction.

DISCLOSURE OF INVENTION

The present invention solves the above stated needs. Once an image is captured digitally, a search of the image determines whether symbolic content is included in the image. If so the symbol is decoded and communication is opened with the proper database, usually using the Internet, wherein the best match for the symbol is returned. In some instances, a symbol may be detected, but non-ambiguous identification is not possible. In that case and when a symbolic image can not be detected, the image is decomposed through identification algorithms where unique characteristics of the image are determined. These characteristics are then used to provide the best match or matches in the data base, the "best" determination being assisted by the partial symbolic information, if that is available.

Therefore the present invention provides technology and processes that can accommodate linking objects and images to information via a network such as the Internet, which requires no modification to the linked object. Traditional methods for linking objects to digital information, including applying a barcode, radio or optical transceiver or transmitter, or some other means of identification to the object, or modifying the image or object so as to encode detectable information in it, are not required because the image or object can be identified solely by its visual appearance. The users or devices may even interact with objects by "linking" to them. For example, a user may link to a vending machine by "pointing and clicking" on it. His device would be connected over the Internet to the company that owns the vending machine. The company would in turn establish a connection to the vending machine, and thus the user would have a communication channel established with the vending machine and could interact with it.

The decomposition algorithms of the present invention allow fast and reliable detection and recognition of images and/or objects based on their visual appearance in an image, no matter whether shadows, reflections, partial obscuration, and variations in viewing geometry are present. As stated above, the present invention also can detect, decode, and identify images and objects based on traditional symbols which may appear on the object, such as alphanumeric characters, barcodes, or 2-dimensional matrix codes.

When a particular object is identified, the position and orientation of an object with respect to the user at the time the image was captured can be determined based on the appearance of the object in an image. This can be the location and/or identity of people scanned by multiple cameras in a security system, a passive locator system more accurate than GPS or usable in areas where GPS signals cannot be received, the location of specific vehicles without requiring a transmission from the vehicle, and many other uses.

When the present invention is incorporated into a mobile device, such as a portable telephone, the user of the device can link to images and objects in his or her environment by pointing the device at the object of interest, then "pointing and clicking" to capture an image. Thereafter, the device transmits the image to another computer ("Server"), wherein the image is analyzed and the object or image of interest is detected and recognized. Then the network address of information corresponding to that object is transmitted from the ("Server") back to the mobile device, allowing the mobile device to access information using the network address so that only a portion of the information concerning the object need be stored in the systems database.

Some or all of the image processing, including image/object detection and/or decoding of symbols detected in the image may be distributed arbitrarily between the mobile (Client) device and the Server. In other words, some processing may be performed in the Client device and some in the Server, without specification of which particular processing is performed in each, or all processing may be performed on one platform or the other, or the platforms may be combined so that there is only one platform. The image processing can be implemented in a parallel computing manner, thus facilitating scaling of the system with respect to database size and input traffic loading.

Therefore, it is an object of the present invention to provide a system and process for identifying digitally captured images without requiring modification to the object.

Another object is to use digital capture devices in ways never contemplated by their manufacturer.

Another object is to allow identification of objects from partial views of the object.

Another object is to provide communication means with operative devices without requiring a public connection therewith.

These and other objects and advantages of the present invention will become apparent to those skilled in the art after considering the following detailed specification, together with the accompanying drawings wherein:

BRIEF DESCRIPTION OF THE DRAWINGS

FIG. 2 is an idealized view of image capture;

BEST MODES FOR CARRYING OUT THE INVENTION

The present invention includes a novel process whereby information such as Internet content is presented to a user, based solely on a remotely acquired image of a physical object. Although coded information can be included in the remotely acquired image, it is not required since no additional information about a physical object, other than this image, needs to be encoded in the linked object. There is no need for any additional code or device, radio, optical or otherwise, to be embedded in or affixed to the object. Image-linked objects can be located and identified within user-acquired imagery solely by means of digital image processing, with the address of pertinent information being returned to the device used to acquire the image and perform the link. This process is robust against digital image noise and corruption (as can result from lossy image compression/decompression), perspective error, rotation, translation, scale differences, illumination variations caused by different lighting sources, and partial obscuration of the target that results from shadowing, reflection or blockage.

Figure 1:
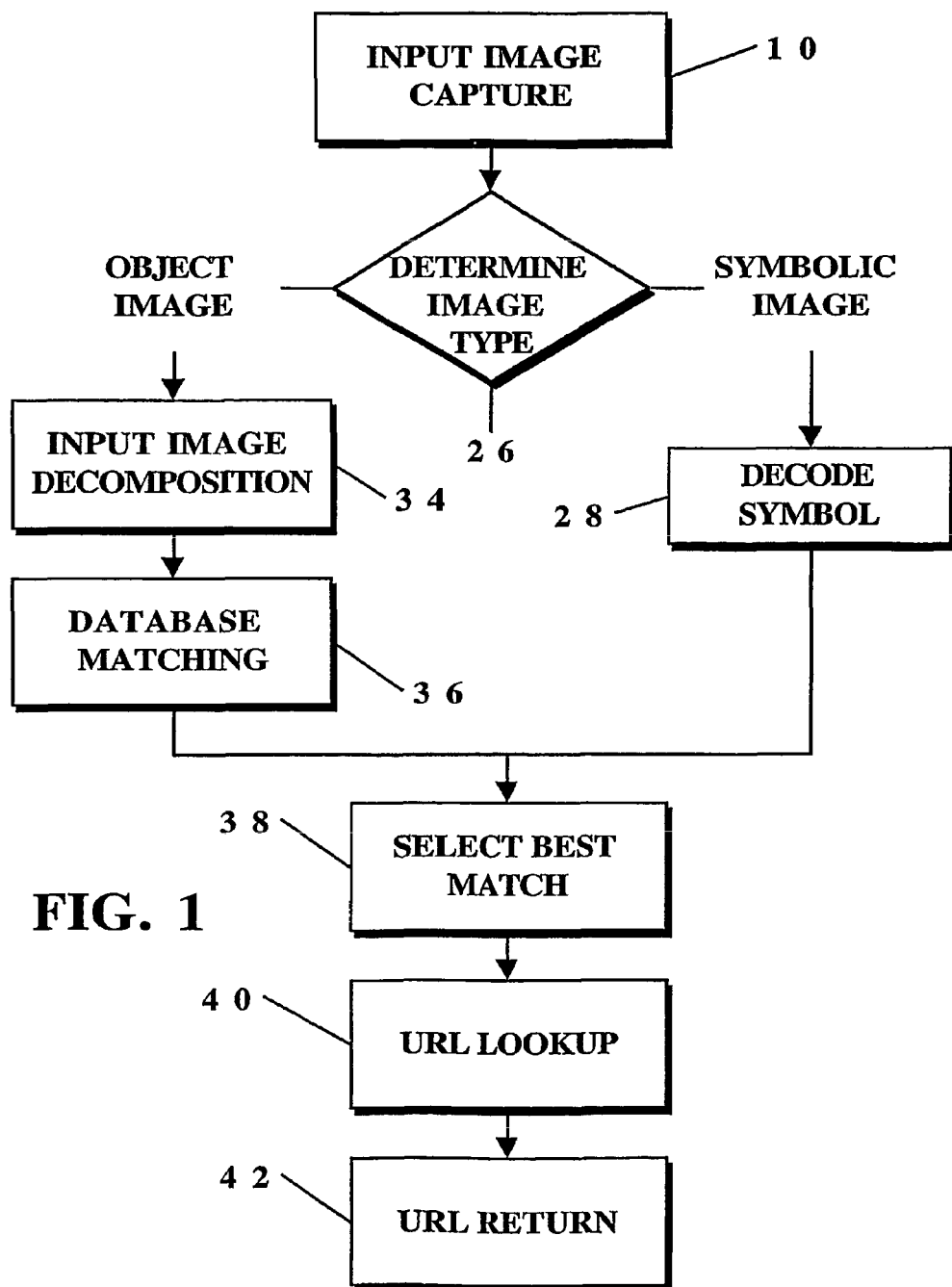
FIG. 1 is a schematic block diagram top-level algorithm flowchart.

Many different variations on machine vision "target location and identification" exist in the current art. However, they all tend to provide optimal solutions for an arbitrarily restricted search space. At the heart of the present invention is a high-speed image matching engine that returns unambiguous matches to target objects contained in a wide variety of potential input images. This unique approach to image matching takes advantage of the fact that at least some portion of the target object will be found in the user-acquired image. The parallel image comparison processes embodied in the present search technique are, when taken together, unique to the process. Further, additional refinement of the process, with the inclusion of more and/or different decomposition-parameterization functions, utilized within the overall structure of the search loops is not restricted. The detailed process is described in the following. FIG. 1 shows the overall processing flow and steps. These steps are described in further detail in the following sections.

For image capture 10, the User 12 (FIG. 2) utilizes a computer, mobile telephone, personal digital assistant, or other similar device 14 equipped with an image sensor (such as a CCD or CMOS digital camera). The User 12 aligns the sensor of the image capture device 14 with the object 16 of interest. The linking process is then initiated by suitable means including: the User 12 pressing a button on the device 14 or sensor; by the software in the device 14 automatically recognizing that an image is to be acquired; by User voice command; or by any other appropriate means. The device 14 captures a digital image 18 of the scene at which it is pointed. This image 18 is represented as three separate 2-D matrices of pixels, corresponding to the raw RGB (Red, Green, Blue) representation of the input image. For the purposes of standardizing the analytical processes in this embodiment, if the device 14 supplies an image in other than RGB format, a transformation to RGB is accomplished. These analyses could be carried out in any standard color format, should the need arise.

If the server 20 is physically separate from the device 14, then user acquired images are transmitted from the device 14 to the Image Processor/Server 20 using a conventional digital network or wireless network means. If the image 18 has been compressed (e.g. via lossy JPEG DCT) in a manner that introduces compression artifacts into the reconstructed image 18, these artifacts may be partially removed by, for example, applying a conventional despeckle filter to the reconstructed image prior to additional processing.

The Image Type Determination 26 is accomplished with a discriminator algorithm which operates on the input image 18 and determines whether the input image contains recognizable symbols, such as barcodes, matrix codes, or alphanumeric characters. If such symbols are found, the image 18 is sent to the Decode Symbol 28 process. Depending on the confidence level with which the discriminator algorithm finds the symbols, the image 18 also may or alternatively contain an object of interest and may therefore also or alternatively be sent to the Object Image branch of the process flow. For example, if an input image 18 contains both a barcode and an object, depending on the clarity with which the barcode is detected, the image may be analyzed by both the Object Image and Symbolic Image branches, and that branch which has the highest success in identification will be used to identify and link from the object.

The image is analyzed to determine the location, size, and nature of the symbols in the Decode Symbol 28. The symbols are analyzed according to their type, and their content information is extracted. For example, barcodes and alphanumeric characters will result in numerical and/or text information.

For object images, the present invention performs a "decomposition", in the Input Image Decomposition 34, of a high-resolution input image into several different types of quantifiable salient parameters. This allows for multiple independent convergent search processes of the database to occur in parallel, which greatly improves image match speed and match robustness in the Database Matching 36. The Best Match 38 from either the Decode Symbol 28, or the image Database Matching 36, or both, is then determined. If a specific URL (or other online address) is associated with the image, then an URL Lookup 40 is performed and the Internet address is returned by the URL Return 42.

The overall flow of the Input Image Decomposition process is as follows:

---

Radiometric Correction
Segmentation
Segment Group Generation
FOR each segment group
   Bounding Box Generation
   Geometric Normalization
   Wavelet Decomposition
   Color Cube Decomposition
   Shape Decomposition
   Low-Resolution Grayscale Image Generation
FOR END

---

Each of the above steps is explained in further detail below. For Radiometric Correction, the input image typically is transformed to an 8-bit per color plane, RGB representation. The RGB image is radiometrically normalized in all three channels. This normalization is accomplished by linear gain and offset transformations that result in the pixel values within each color channel spanning a full 8-bit dynamic range (256 possible discrete values). An 8-bit dynamic range is adequate but, of course, as optical capture devices produce higher resolution images and computers get faster and memory gets cheaper, higher bit dynamic ranges, such as 16-bit, 32-bit or more may be used.

For Segmentation, the radiometrically normalized RGB image is analyzed for "segments," or regions of similar color, i.e. near equal pixel values for red, green, and blue. These segments are defined by their boundaries, which consist of sets of (x, y) point pairs. A map of segment boundaries is produced, which is maintained separately from the RGB input image and is formatted as an x, y binary image map of the same aspect ratio as the RGB image.

For Segment Group Generation, the segments are grouped into all possible combinations. These groups are known as "segment groups" and represent all possible potential images or objects of interest in the input image. The segment groups are sorted based on the order in which they will be evaluated. Various evaluation order schemes are possible. The particular embodiment explained herein utilizes the following "center-out" scheme: The first segment group comprises only the segment that includes the center of the image. The next segment group comprises the previous segment plus the segment which is the largest (in number of pixels) and which is adjacent to (touching) the previous segment group. Additional segments are added using the segment criteria above until no segments remain. Each step, in which a new segment is added, creates a new and unique segment group.

For Bounding Box Generation, the elliptical major axis of the segment group under consideration (the major axis of an ellipse just large enough to contain the entire segment group) is computed. Then a rectangle is constructed within the image coordinate system, with long sides parallel to the elliptical major axis, of a size just large enough to completely contain every pixel in the segment group.

For Geometric Normalization, a copy of the input image is modified such that all pixels not included in the segment group under consideration are set to mid-level gray. The result is then resampled and mapped into a "standard aspect" output test image space such that the corners of the bounding box are mapped into the corners of the output test image. The standard aspect is the same size and aspect ratio as the Reference images used to create the database.

For Wavelet Decomposition, a grayscale representation of the full-color image is produced from the geometrically normalized image that resulted from the Geometric Normalization step. The following procedure is used to derive the grayscale representation. Reduce the three color planes into one grayscale image by proportionately adding each R, G, and B pixel of the standard corrected color image using the following formula:

$$L_{x,y} = 0.34 * R_{x,y} + 0.55 * G_{x,y} + 0.44 * B_{x,y}$$

then round to nearest integer value. Truncate at 0 and 255, if necessary. The resulting matrix L is a standard grayscale image. This grayscale representation is at the same spatial resolution as the full color image, with an 8-bit dynamic range. A multi-resolution Wavelet Decomposition of the grayscale image is performed, yielding wavelet coefficients for several scale factors. The Wavelet coefficients at various scales are ranked according to their weight within the image.

For Color Cube Decomposition, an image segmentation is performed (see "Segmentation" above), on the RGB image that results from Geometric Normalization. Then the RGB image is transformed to a normalized Intensity, In-phase and Quadrature-phase color image (YIQ). The segment map is used to identify the principal color regions of the image, since each segment boundary encloses pixels of similar color. The average Y, I, and Q values of each segment, and their individual component standard deviations, are computed. The following set of parameters result, representing the colors, color variation, and size for each segment:

$Y_{avg}$=Average Intensity
$I_{avg}$=Average In-phase
$Q_{avg}$=Average Quadrature
$Y_{sigma}$=Intensity standard deviation
$I_{sigma}$=In-phase standard deviation
$Q_{sigma}$=Quadrature standard deviation
$N_{pixels}$=number of pixels in the segment The parameters comprise a representation of the color intensity and variation in each segment. When taken together for all segments in a segment group, these parameters comprise points (or more accurately, regions, if the standard deviations are taken into account) in a three-dimensional color space and describe the intensity and variation of color in the segment group.

For Shape Decomposition, the map resulting from the segmentation performed in the Color Cube Generation step is used and the segment group is evaluated to extract the group outer edge boundary, the total area enclosed by the boundary, and its area centroid. Additionally, the net ellipticity (semi-major axis divided by semi-minor axis of the closest fit ellipse to the group) is determined.

For Low-Resolution Grayscale Image Generation, the full-resolution grayscale representation of the image that was derived in the Wavelet Generation step is now subsampled by a factor in both x and y directions. For the example of this embodiment, a 3:1 subsampling is assumed. The subsampled image is produced by weighted averaging of pixels within each 3×3 cell. The result is contrast binned, by reducing the number of discrete values assignable to each pixel based upon substituting a "binned average" value for all pixels that fall within a discrete (TBD) number of brightness bins.

The above discussion of the particular decomposition methods incorporated into this embodiment are not intended to indicate that more, or alternate, decomposition methods may not also be employed within the context of this invention.

In other words:

```
FOR each input image segment group
    FOR each database object
        FOR each view of this object
            FOR each segment group in this view of this database
                object
                Shape Comparison
                Grayscale Comparison
                Wavelet Comparison
                Color Cube Comparison
                Calculate Combined Match Score
            END FOR
        END FOR
    END FOR
END FOR
```

Each of the above steps is explained in further detail below.

FOR Each Input Image Segment Group

This loop considers each combination of segment groups in the input image, in the order in which they were sorted in the "Segment Group Generation" step. Each segment group, as it is considered, is a candidate for the object of interest in the image, and it is compared against database objects using various tests.

One favored implementation, of many possible, for the order in which the segment groups are considered within this loop is the "center-out" approach mentioned previously in the "Segment Group Generation" section. This scheme considers segment groups in a sequence that represents the addition of adjacent segments to the group, starting at the center of the image. In this scheme, each new group that is considered comprises the previous group plus one additional adjacent image segment. The new group is compared against the database. If the new group results in a higher database matching score than the previous group, then new group is retained. If the new group has a lower matching score then the previous group, then it is discarded and the loop starts again. If a particular segment group results in a match score which is extremely high, then this is considered to be an exact match and no further searching is warranted; in this case the current group and matching database group are selected as the match and this loop is exited.

FOR Each Database Object

This loop considers each object in the database for comparison against the current input segment group.

FOR Each View of this Object

This loop considers each view of the current database object, for comparison against the current input segment group. The database contains, for each object, multiple views from different viewing angles.

FOR Each Segment Group in this View of this Database Object

This loop considers each combination of segment groups in the current view of the database object. These segment groups were created in the same manner as the input image segment groups.

Shape Comparison

Inputs:

For the input image and all database images:

I. Segment group outline

II. Segment group area

III. Segment group centroid location

IV. Segment group bounding ellipse ellipticity

Algorithm:

V. Identify those database segment groups with an area approximately equal to that of the input segment group, within TBD limits, and calculate an area matching score for each of these "matches."

VI. Within the set of matches identified in the previous step, identify those database segment groups with an ellipticity approximately equal to that of the input segment group, within TBD limits, and calculate an ellipticity position matching score for each of these "matches."

Within the set of matches identified in the previous step, identify those database segment groups with a centroid position approximately equal to that of the input segment group, within TBD limits, and calculate a centroid position matching score for each of these "matches."

VIII. Within the set of matches identified in the previous step, identify those database segment groups with an outline shape approximately equal to that of the input segment group, within TBD limits, and calculate an outline matching score for each of these "matches." This is done by comparing the two outlines and analytically determining the extent to which they match.

Note: this algorithm need not necessarily be performed in the order of Steps 1 to 4. It could alternatively proceed as follows:

```
FOR each database segment group
    IF the group passes Step 1
        IF the group passes Step 2
            IF the group passes Step 3
                IF the group passes Step 4
                    Successful comparison, save result
                END IF
            END IF
        END IF
    END IF
END FOR
```

Grayscale Comparison

Inputs:

For the input image and all database images:

IX. Low-resolution, normalized, contrast-binned, grayscale image of pixels within segment group bounding box, with pixels outside of the segment group set to a standard background color.

Algorithm:

Given a series of concentric rectangular "tiers" of pixels within the low-resolution images, compare the input image pixel values to those of all database images. Calculate a matching score for each comparison and identify those database images with matching scores within TBD limits, as follows:

```
FOR each database image
    FOR each tier, starting with the innermost and progressing to the
    outermost
        Compare the pixel values between the input and database image
        Calculate an aggregate matching score
        IF matching score is greater than some TBD limit (i.e., close match)
            Successful comparison, save result
        END IF
    END FOR
END FOR
```

Wavelet Comparison

Inputs:

For the input image and all database images:

X. Wavelet coefficients from high-resolution grayscale image within segment group bounding box.

Algorithm:

Successively compare the wavelet coefficients of the input segment group image and each database segment group image, starting with the lowest-order coefficients and progressing to the highest order coefficients. For each comparison, compute a matching score. For each new coefficient, only consider those database groups that had matching scores, at the previous (next lower order) coefficient within TBD limits.

```
FOR each database image
    IF input image C_0 equals database image C_0 within TBD limit
        IF input image C_1 equals database image C_1 within TBD limit
            IF input image C_N equals database image C_N within TBD
            limit
                Close match, save result and match score
            END IF
        END IF
    END IF
END FOR
```

Notes:

I. "$C_i$" are the wavelet coefficients, with $C_0$ being the lowest order coefficient and $C_N$ being the highest.

II. When the coefficients are compared, they are actually compared on a statistical (e.g. Gaussian) basis, rather than an arithmetic difference.

III. Data indexing techniques are used to allow direct fast access to database images according to their $C_i$ values. This allows the algorithm to successively narrow the portions of the database of interest as it proceeds from the lowest order terms to the highest.

Color Cube Comparison
Inputs:
[$Y_{avg}$, $I_{avg}$, $Q_{avg}$, $Y_{Sigma}$, $I_{sigma}$, $Q_{sigma}$, $N_{pixels}$] data sets ("Color Cube Points") for each segment in:
  I. The input segment group image
  II. Each database segment group image
Algorithm:

```
FOR each database image
   FOR each segment group in the database image
      FOR each Color Cube Point in database segment group, in order of
      descending N_pixels value
         IF Gaussian match between input (Y,I,Q) and database
         (Y,I,Q)
            I. Calculate match score for this segment
            II. Accumulate segment match score into aggregate match
            score for segment group
            III. IF aggregate matching score is greater than some TBD
            limit (i.e., close match)
               Successful comparison, save result
         END IF
      END FOR
   END FOR
END FOR
```

Calculate Combined Match Score

The four Object Image comparisons (Shape Comparison, Grayscale Comparison, Wavelet Comparison, Color Cube Comparison) each return a normalized matching score. These are independent assessments of the match of salient features of the input image to database images. To minimize the effect of uncertainties in any single comparison process, and to thus minimize the likelihood of returning a false match, the following root sum of squares relationship is used to combine the results of the individual comparisons into a combined match score for an image:

$$\text{CurrentMatch} = \text{SQRT}(W_{OC}M_{OC}^2 + W_{CCC}M_{CCC}^2 + W_{WC}M_{WC}^2 + W_{SGC}M_{SGC}^2)$$

where Ws are TBD parameter weighting coefficients and Ms are the individual match scores of the four different comparisons.

The unique database search methodology and subsequent object match scoring criteria are novel aspects of the present invention that deserve special attention. Each decomposition of the Reference image and Input image regions represent an independent characterization of salient characteristics of the image. The Wavelet Decomposition, Color Cube Decomposition, Shape Decomposition, and evaluation of a sub-sampled low-resolution Grayscale representation of an input image all produce sets of parameters that describe the image in independent ways. Once all four of these processes are completed on the image to be tested, the parameters provided by each characterization are compared to the results of identical characterizations of the Reference images, which have been previously calculated and stored in the database. These comparisons, or searches, are carried out in parallel. The result of each search is a numerical score that is a weighted measure of the number of salient characteristics that "match" (i.e. that are statistically equivalent). Near equivalencies are also noted, and are counted in the cumulative score, but at a significantly reduced weighting.

One novel aspect of the database search methodology in the present invention is that not only are these independent searches carried out in parallel, but also, all but the low-resolution grayscale compares are "convergent." By convergent, it is meant that input image parameters are searched sequentially over increasingly smaller subsets of the entire database. The parameter carrying greatest weight from the input image is compared first to find statistical matches and near-matches in all database records. A normalized interim score (e.g., scaled value from zero to one, where one is perfect match and zero is no match) is computed, based on the results of this comparison. The next heaviest weighted parameter from the input image characterization is then searched on only those database records having initial interim scores above a minimum acceptable threshold value. This results in an incremental score that is incorporated into the interim score in a cumulative fashion. Then, subsequent compares of increasingly lesser-weighted parameters are assessed only on those database records that have cumulative interim scores above the same minimum acceptable threshold value in the previous accumulated set of tests.

This search technique results in quick completion of robust matches, and establishes limits on the domain of database elements that will be compared in a subsequent combined match calculation and therefore speeds up the process. The convergent nature of the search in these comparisons yields a ranked subset of the entire database.

The result of each of these database comparisons is a ranking of the match quality of each image, as a function of decomposition search technique. Only those images with final cumulative scores above the acceptable match threshold will be assessed in the next step, a Combined Match Score evaluation.

Four database comparison processes, Shape Comparison, Grayscale Comparison, Wavelet Comparison, and Color Cube Comparison, are performed. These processes may occur sequentially, but generally are preferably performed in parallel on a parallel computing platform. Each comparison technique searches the entire image database and returns those images that provide the best matches, for the particular algorithm, along with the matching scores for these images. These comparison algorithms are performed on segment groups, with each input image segment group being compared to each segment group for each database image.

Figure 3A:
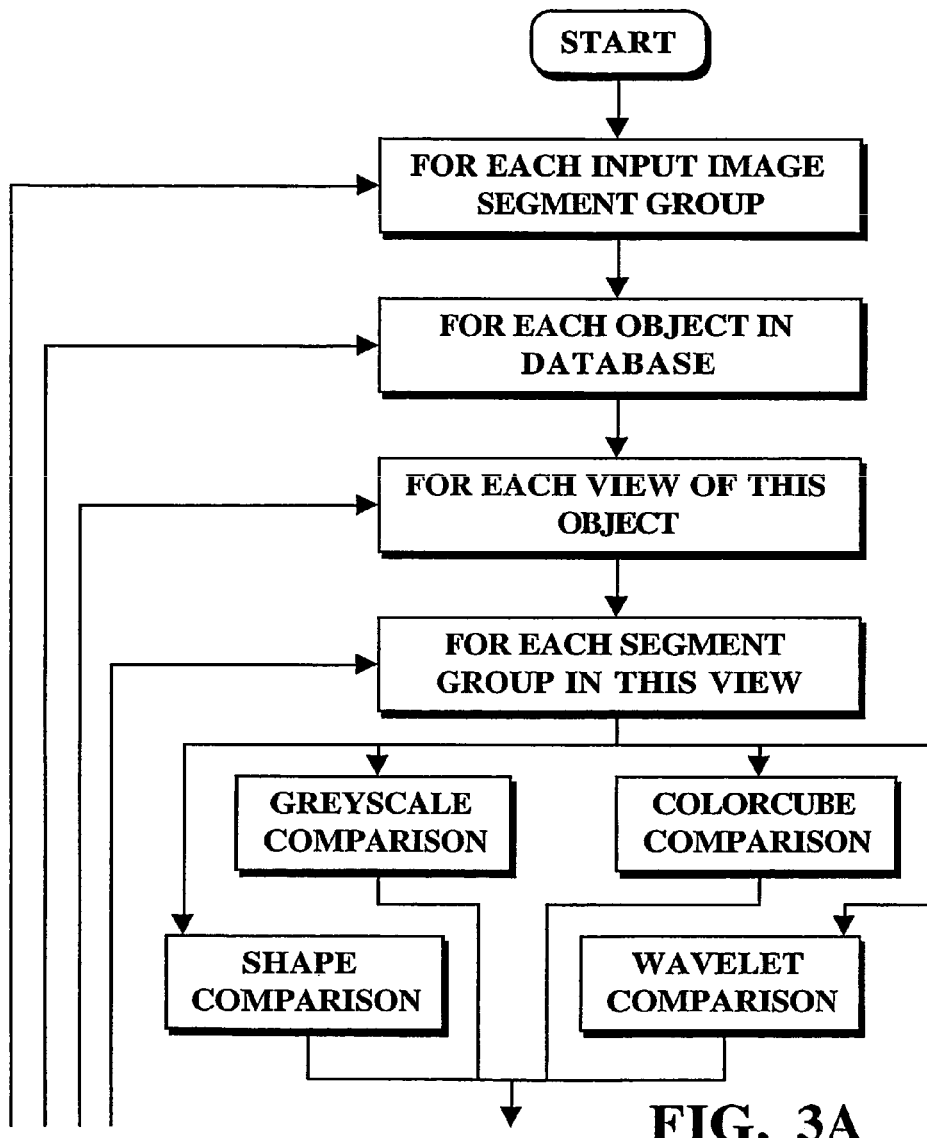
FIGS. 3A and 3B are a schematic block diagram of process details of the present invention.
Figure 3B:
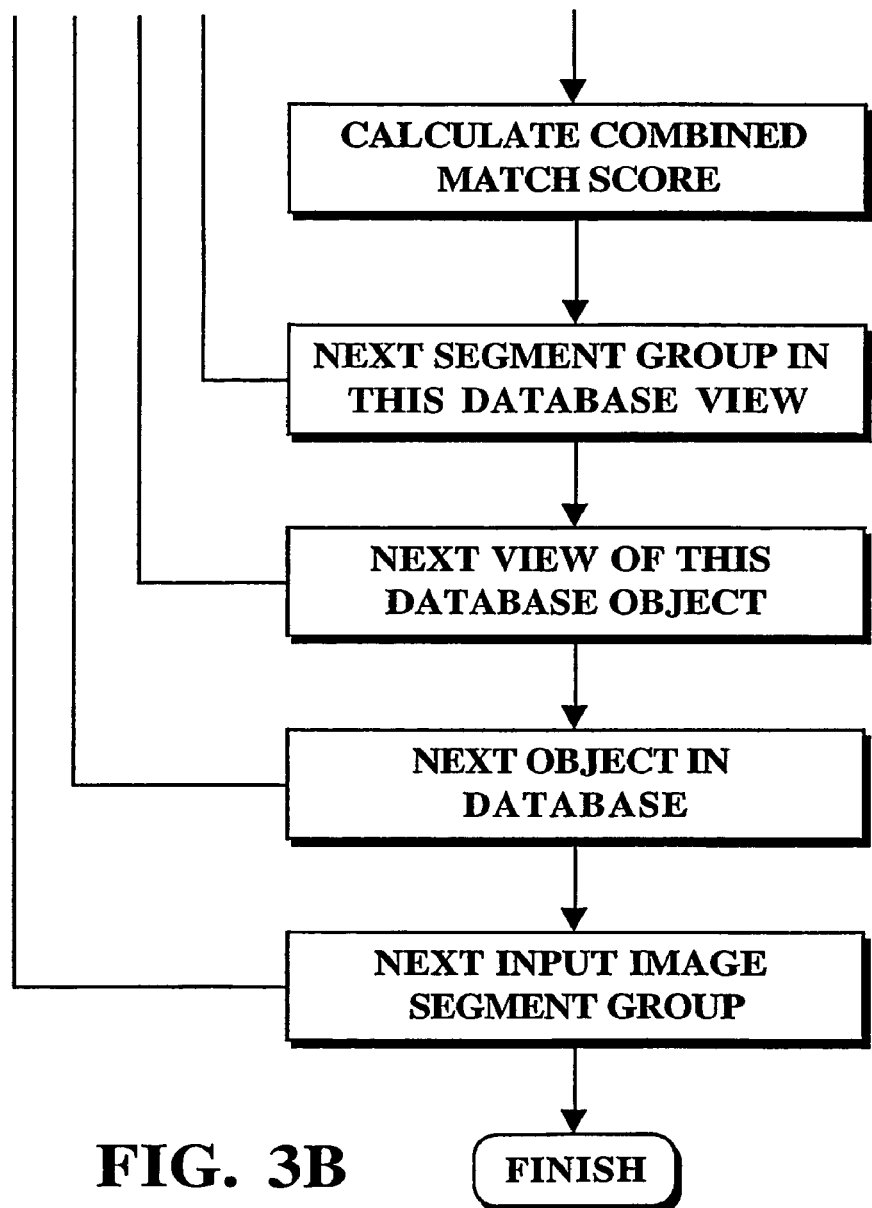

FIGS. 3A and 3B show the process flow within the Database Matching operation. The algorithm is presented here as containing four nested loops with four parallel processes inside the innermost loop. This structure is for presentation and explanation only. The actual implementation, although performing the same operations at the innermost layer, can have a different structure in order to achieve the maximum benefit from processing speed enhancement techniques such as parallel computing and data indexing techniques. It is also important to note that the loop structures can be implemented independently for each inner comparison, rather than the shared approach shown in the FIGS. 3A and 3B.

Preferably, parallel processing is used to divide tasks between multiple CPUs (Central Processing Units) and/or computers. The overall algorithm may be divided in several ways, such as:

Sharing the Outer Loop: In this technique, all CPUs run the entire algorithm, including the outer loop, but one CPU runs the loop for the first N cycles, another CPU for the second N cycles, all simultaneously.
  Sharing the Comparisons: In this technique, one CPU performs the loop functions. When the comparisons are performed, they are each passed to a separate CPU to be performed in parallel.
  Sharing the Database: This technique entails splitting database searches between CPUs, so that each CPU is responsible for searching one section of the database, and the sections are searched in parallel by multiple CPUs. This is, in essence, a form of the "Sharing the Outer Loop" technique described above.

Actual implementations can be some combination of the above techniques that optimizes the process on the available hardware.

Another technique employed to maximize speed is data indexing. This technique involves using a priori knowledge of where data resides to only search in those parts of the database that contain potential matches. Various forms of indexing may be used, such as hash tables, data compartmentalization (i.e., data within certain value ranges are stored in certain locations), data sorting, and database table indexing. An example of such techniques is, in the Shape Comparison algorithm (see below), if a database is to be searched for an entry with an Area with a value of A, the algorithm would know which database entries or data areas have this approximate value and would not need to search the entire database.

Figure 4:
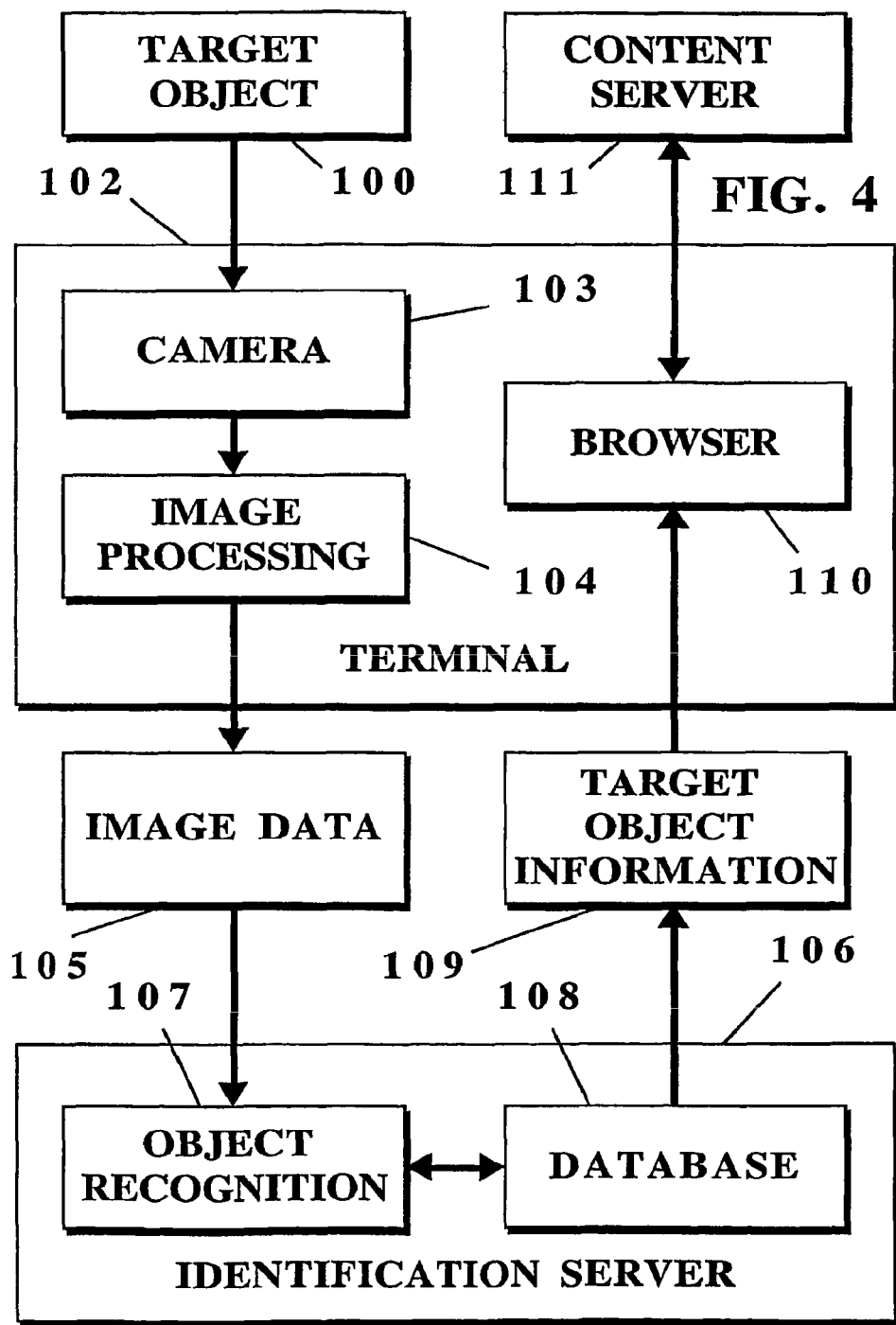
FIG. 4 is a schematic block diagram of a different explanation of invention.

Another technique employed is as follows. FIG. 4 shows a simplified configuration of the invention. Boxes with solid lines represent processes, software, physical objects, or devices. Boxes with dashed lines represent information. The process begins with an object of interest: the target object 100. In the case of consumer applications, the target object 100 could be, for example, beverage can, a music CD box, a DVD video box, a magazine advertisement, a poster, a theatre, a store, a building, a car, or any other object that user is interested in or wishes to interact with. In security applications the target object 100 could be, for example, a person, passport, or driver's license, etc. In industrial applications the target object 100 could be, for example, a part in a machine, a part on an assembly line, a box in a warehouse, or a spacecraft in orbit, etc.

The terminal 102 is a computing device that has an "image" capture device such as digital camera 103, a video camera, or any other device that an convert a physical object into a digital representation of the object. The imagery can be a single image, a series of images, or a continuous video stream. For simplicity of explanation this document describes the digital imagery generally in terms of a single image, however the invention and this system can use all of the imagery types described above.

After the camera 103 captures the digital imagery of the target object 100, image preprocessing 104 software converts the digital imagery into image data 105 for transmission to and analysis by an identification server 106. Typically a network connection is provided capable of providing communications with the identification server 106. Image data 105 is data extracted or converted from the original imagery of the target object 100 and has information content appropriate for identification of the target object 100 by the object recognition 107, which may be software or hardware. Image data 105 can take many forms, depending on the particular embodiment of the invention. Examples of image data 105 are:

Compressed (e.g., JPEG2000) form of the raw imagery from camera 103;

Key image information, such as spectral and/or spatial frequency components (e.g. wavelet components) of the raw imagery from camera 103; and MPEG video stream created from the raw imagery from camera 103.

The particular form of the image data 105 and the particular operations performed in image preprocessing 104 depend on:

Algorithm and software used in object recognition 107
Processing power of terminal 102;

Network connection speed between terminal 102 and identification server 106;

Application of the System; and

Required system response time.

In general, there is a tradeoff between the network connection speed (between terminal 102 and identification server 106) and the processing power of terminal 102. The results all of the above tradeoffs will define the nature of image preprocessing 104 and image data 105 for a specific embodiment. For example, image preprocessing 104 could be image compression and image data 105 compressed imagery, or image preprocessing 104 could be wavelet analysis and image data 105 could be wavelet coefficients.

The image data 105 is sent from the terminal 102 to the identification server 106. The identification server 106 receives the image data 105 and passes it to the object recognition 107.

The identification server 106 is a set of functions that usually will exist on computing platform separate from the terminal 102, but could exist on the same computing platform. If the identification server 106 exists on a separate computing device, such as a computer in a data center, then the transmission of the image components 105 to the identification server 106 is accomplished via a network or combination of networks, such a cellular telephone network, wireless Internet, Internet, and wire line network. If the identification server 106 exists on the same computing device as the terminal 102 then the transmission consists simply of a transfer of data from one software component or process to another.

Placing the identification server 106 on a computing platform separate from the terminal 102 enables the use of powerful computing resources for the object recognition 107 and database 108 functions, thus providing the power of these computing resources to the terminal 102 via network connection. For example, an embodiment that identifies objects out of a database of millions of known objects would be facilitated by the large storage, memory capacity, and processing power available in a data center; it may not be feasible to have such computing power and storage in a mobile device. Whether the terminal 102 and the identification server 106 are on the same computing platform or separate ones is an architectural decision that depends on system response time, number of database records, image recognition algorithm computing power and storage available in terminal 102, etc., and this decision must be made for each embodiment of the invention. Based on current technology, in most embodiments these functions will be on separate computing platforms.

The overall function of the identification server 106 is to determine and provide the target object information 109 corresponding to the target object 100, based on the image data 105.

The object recognition 107 and the database 108 function together to:

1. Detect, recognize, and decode symbols, such as barcodes or text, in the image.

2. Recognize the object (the target object 100) in the image.

3. Provide the target object information 109 that corresponds to the target object 100. The target object information 109 usually (depending on the embodiment) includes an information address corresponding to the target object 100.

The object recognition 107 detects and decodes symbols, such as barcodes or text, in the input image. This is accomplished via algorithms, software, and/or hardware components suited for this task. Such components are commercially available (The HALCON software package from MVTec is an example). The object recognition 107 also detects and recognizes images of the target object 100 or portions thereof.

This is accomplished by analyzing the image data 105 and comparing the results to other data, representing images of a plurality of known objects, stored in the database 108, and recognizing the target object 100 if a representation of target object 100 is stored in the database 108.

In some embodiments the terminal 102 includes software, such as a web browser (the browser 110), that receives an information address, connects to that information address via a network or networks, such as the Internet, and exchanges information with another computing device at that information address. In consumer applications the terminal 102 may be a portable cellular telephone or Personal Digital Assistant equipped with a camera 103 and wireless Internet connection. In security and industrial applications the terminal 102 may be a similar portable hand-held device or may be fixed in location and/or orientation, and may have either a wireless or wire line network connection.

Other object recognition techniques also exist and include methods that store 3-dimensional models (rather than 2-dimensional images) of objects in a database and correlate input images with these models of the target object is performed by an object recognition technique of which many are available commercially and in the prior art. Such object recognition techniques usually consist of comparing a new input image to a plurality of known images and detecting correspondences between the new input image and one of more of the known images. The known images are views of known objects from a plurality of viewing angles and thus allow recognition of 2-dimensional and 3-dimensional objects in arbitrary orientations relative to the camera 103.

FIG. 4 shows the object recognition 107 and the database 108 as separate functions for simplicity. However, in many embodiments the object recognition 107 and the database 108 are so closely interdependent that they may be considered a single process.

There are various options for the object recognition technique and the particular processes performed within the object recognition 107 and the database 108 depend on this choice. The choice depends on the nature, requirements, and architecture of the particular embodiment of the invention. However, most embodiments will usually share most of the following desired attributes of the image recognition technique:

Capable of recognizing both 2-dimensional (i.e., flat) and 3-dimensional objects;

Capable of discriminating the target object 100 from any foreground or background objects or image information, i.e., be robust with respect to changes in background;

Fast;

Autonomous (no human assistance required in the recognition process);

Scalable; able to identify objects from a large database of known objects with short response time; and Robust with respect to:

Affine transformations (rotation, translation, scaling);

Non-affine transformations (stretching, bending, breaking);

Occlusions (of the target object 100);

Shadows (on the target object 100);

Reflections (on the target object 100);

Variations in light color temperature;

Image noise;

Capable of determining position and orientation of the target object 100 in the original imagery; and Capable of recognizing individual human faces from a database containing data representing a large plurality of human faces.

All of these attributes do not apply to all embodiments. For example, consumer linking embodiments generally do not require determination of position and orientation of the target object 100, while a spacecraft target position and orientation determination system generally would not be required to identify human faces or a large number of different objects.

It is usually desirable that the database 108 be scalable to enable identification of the target object 100 from a very large plurality (for example, millions) of known objects in the database 108. The algorithms, software, and computing hardware must be designed to function together to quickly perform such a search. An example software technique for performing such searching quickly is to use a metric distance comparison technique for comparing the image data 105 to data stored in the database 108, along with database clustering and multiresolution distance comparisons. This technique is described in "Fast Exhaustive Multi-Resolution Search Algorithm Based on Clustering for Efficient Image Retrieval," by Song, Kim, and Ra, 2000.

In addition to such software techniques, a parallel processing computing architecture may be employed to achieve fast searching of large databases. Parallel processing is particularly important in cases where a non-metric distance is used in object recognition 107, because techniques such database clustering and multiresolution search may not be possible and thus the complete database must be searched by partitioning the database across multiple CPUs.

As described above, the object recognition 107 can also detect identifying marks on the target object 100. For example, the target object 100 may include an identifying number or a barcode. This information can be decoded and used to identify or help identify the target object 100 in the database 108. This information also can be passed on as part of the target object information 109. If the information is included as part of the target object information 109 then it can be used by the terminal 102 or content server 111 to identify the specific target object 100, out of many such objects that have similar appearance and differ only in the identifying marks. This technique is useful, for example, in cases where the target object 100 is an active device with a network connection (such as a vending machine) and the content server establishes communication with the target object 100. A combination with a Global Positioning System can also be used to identify like objects by their location.

The object recognition 107 may be implemented in hardware, software, or a combination of both. Examples of each category are presented below.

Hardware object recognition implementations include optical correlators, optimized computing platforms, and custom hardware.

Optical correlators detect objects in images very rapidly by, in effect, performing image correlation calculations with light. Examples of optical correlators are:

Litton Miniaturized Ruggedized Optical Correlator, from Northrop Grumman Corp;

Hybrid Digital/Optical Correlator, from the School of Engineering and Information Technology, University of Sussex, UK; and OC-VGA3000 and OC-VGA6000 Optical Correlators from INO, Quebec, Canada.

Optimized computing platforms are hardware computing systems, usually on a single board, that are optimized to perform image processing and recognition algorithms very quickly. These platforms must be programmed with the object recognition algorithm of choice. Examples of optimized computing platforms are:

VIP/Balboa™ Image Processing Board, from Irvine Sensors Corp.; and

3DANN™-R Processing System, from Irvine Sensors Corp.

Image recognition calculations can also be implemented directly in custom hardware in forms such as Application Specific Integrated Circuits (ASICs), Field Programmable Gate Arrays (FPGAs), and Digital Signal Processors (DSPs).

There are many object and image recognition software applications available commercially and many algorithms published in the literature. Examples of commercially available image/object recognition software packages include:

Object recognition system, from Sandia National Laboratories;

Object recognition perception modules, from Evolution Robotics;

ImageFinder, from Attrasoft;

ImageWare, from Roz Software Systems; and

ID-2000, from Imagis Technologies.

Some of the above recognition systems include 3-dimensional object recognition capability while others perform 2-dimensional image recognition. The latter type are used to perform 3-dimensional object recognition by comparing input images to a plurality of 2-dimensional views of objects from a plurality of viewing angles.

Examples of object recognition algorithms in the literature and intended for implementation in software are:

Distortion Invariant Object Recognition in the Dynamic Link Architecture, Lades et al, 1993;

SEEMORE: Combining Color, Shape, and Texture Histogramming in a Neurally Inspired Approach to Visual Object Recognition, Mel, 1996;

Probabilistic Affine Invariants for Recognition, Leung et al, 1998;

Software Library for Appearance Matching (SLAM), Nene at al, 1994;

Probabilistic Models of Appearance for 3-D Object Recognition, Pope & Lowe, 2000;

Matching 3D Models with Shape Distributions, Osada et al, 2001;

Finding Pictures of Objects in Large Collections of Images, Forsyth et al, 1996;

The Earth Mover's Distance under Transformation Sets, Cohen & Guibas, 1999;

Object Recognition from Local Scale-Invariant Features, Lowe, 1999; and

Fast Object Recognition in Noisy Images Using Simulated Annealing, Betke & Makris, 1994.

Part of the current invention is the following object recognition algorithm specifically designed to be used as the object recognition 107 and, to some extent, the database 108. This algorithm is robust with respect to occlusions, reflections, shadows, background/foreground clutter, object deformation and breaking, and is scalable to large databases. The task of the algorithm is to find an object or portion thereof in an input image, given a database of multiple objects with multiple views (from different angles) of each object.

This algorithm uses the concept of a Local Image Descriptor (LID) to summarize the information in a local region of an image. A LID is a circular subset, or "cutout," of a portion of an image. There are various formulations for LIDs; two examples are:

LID Formulation 1

The area within the LID is divided into range and angle bins. The average color in each [range,angle] bin is calculated from the pixel values therein.

LID Formulation 2

The area within the LID is divided into range bins. The color histogram values within each range bin are calculated from the pixel values therein. For each range bin, a measure of the variation of color with angle is calculated as, for example, the sum of the changes in average color between adjacent small angular slices of a range bin.

A LID in the input image is compared to a LID in a database image by a comparison technique such the L1 Distance, L2 Distance, Unfolded Distance, Earth Mover Distance, or cross-correlation. Small distances indicate a good match between the portions of the images underlying the LIDS. By iteratively changing the position and size of the LIDs in the input and database images the algorithm converges on the best match between circular regions in the 2 images.

Limiting the comparisons to subsets (circular LIDs) of the images enables the algorithm to discriminate an object from the background. Only LIDs that fall on the object, as opposed to the background, yield good matches with database images. This technique also enable matching of partially occluded objects; a LID that falls on the visible part of an occluded object will match to a LID in the corresponding location in the database image of the object.

The iteration technique used to find the best match is simulated annealing, although genetic search, steepest descent, or other similar techniques appropriate for multivariable optimization can also be used individually or in combination with simulated annealing. Simulated annealing is modeled after the concept of a molten substance cooling and solidifying into a solid. The algorithm starts at a given temperature and then the temperature is gradually reduced with time. At each time step, the values of the search variables are perturbed from the their previous values to a create a new "child" generation of LIDs. The perturbations are calculated statistically and their magnitudes are functions of the temperature. As the temperature decreases the perturbations decrease in size. The child LIDs, in the input and database images, are then compared. If the match is better than that obtained with the previous "parent" generation, then a statistical decision is made regarding to whether to accept or reject the child LIDs as the current best match. This is a statistical decision that is a function of both the match distance and the temperature. The probability of child acceptance increases with temperature and decreases with match distance. Thus, good matches (small match distance) are more likely to be accepted but poor matches can also be accepted occasionally. The latter case is more likely to occur early in the process when the temperature is high. Statistical acceptance of poor matches is included to allow the algorithm to "jump" out of local minima.

When LID Formulation 1 is used, the rotation angle of the LID need not necessarily be a simulated annealing search parameter. Faster convergence can be obtained by performing a simple step-wise search on rotation to find the best orientation (within the tolerance of the step size) within each simulated annealing time step.

The search variables, in both the input and database images, are:

LID x-position;
LID y-position;
LID radius;
LID x-stretch;
LID y-stretch; and
LID orientation angle (only for LID Formulation 1).

LID x-stretch and LID y-stretch are measures of "stretch" distortion applied to the LID circle, and measure the distortion of the circle into an oval. This is included to provide robustness to differences in orientation and curvature between the input and database images.

The use of multiple simultaneous LIDs provides additional robustness to occlusions, shadows, reflections, rotations, deformations, and object breaking. The best matches for multiple input image LIDS are sought throughout the database images. The input image LIDS are restricted to remain at certain minimum separation distances from each other. The minimum distance between any 2 LIDs centers is a function of the LID radii. The input image LIDS converge and settle on the regions of the input image having the best correspondence to any regions of any database images. Thus the LIDs behave in the manner of marbles rolling towards the lowest spot on a surface, e.g., the bottom of a bowl, but being held apart by their radius (although LIDS generally have minimum separation distances that are less than their radii).

In cases where the object in the input image appears deformed or curved relative to the known configuration in which it appears in the database, multiple input image LIDS will match to different database images. Each input image LID will match to that database image which shows the underlying portion of the object as it most closely resembles the input image. If the input image object is bent, e.g., a curved poster, then one part will match to one database orientation and another part will match to a different orientation.

In the case where the input image object appears to be broken into multiple pieces, either due to occlusion or to physical breakage, use of multiple LIDs again provides robust matching: individual LIDs "settle" on portions of the input image object as they match to corresponding portions of the object in various views in the database.

Robustness with respect to shadows and reflections is provided by LIDs simply not detecting good matches on these input image regions. They are in effect accommodated in the same manner as occlusions.

Robustness with respect to curvature and bending is accommodated by multiple techniques. First, use of multiple LIDs provides such robustness as described above. Secondly, curvature and bending robustness is inherently provided to some extent within each LID by use of LID range bin sizes that increase with distance from the LID center (e.g., logarithmic spacing). Given matching points in an input image and database image, deformation of the input image object away from the plane tangent at the matching point increases with distance from the matching point. The larger bin sizes of the outer bins (in both range and angle) reduce this sensitivity because they are less sensitive to image shifts.

Robustness with respect to lighting color temperature variations is provided by normalization of each color channel within each LID.

Fast performance, particular with large databases, can be obtained through several techniques, as follows:

1. Use of LID Formulation 2 can reduce the amount of search by virtue of being rotationally invariant, although this comes at the cost of some robustness due to loss of image information.

2. If a metric distance (e.g., L1, L2, or Unfolded) is used for LID comparison, then database clustering, based on the triangle inequality, can be used to rule out large portions of the database from searching. Since database LIDs are created during the execution of the algorithm, the run-time database LIDs are not clustered. Rather, during preparation of the database, sample LIDs are created from the database images by sampling the search parameters throughout their valid ranges. From this data, bounding clusters can be created for each image and for portions of images. With this information the search algorithm can rule out portions of the search parameter space.

3. If a metric distance is used, then progressive multiresolution search can be used. This technique saves time by comparing data first at low resolution and only proceeds with successive higher-resolution comparison on candidates with correlations better than the current best match. A discussion of this technique, along with database clustering, can be found in "Fast Exhaustive Multi-Resolution Search Algorithm Based on Clustering for Efficient Image Retrieval," by Song et al, 2000.

4. The parameter search space and number of LIDs can be limited. Bounds can be placed, for example, on the sizes of LIDs depending on the expected sizes of input image objects relative to those in the database. A small number of LIDs, even 1, can be used, at the expense of some robustness.

5. LIDs can be fixed in the database images. This eliminates iterative searching on database LID parameters, at the expense of some robustness.

6. The "x-stretch" and "y-stretch" search parameters can be eliminated, although there is a trade-off between these search parameters and the number of database images. These parameters increase the ability to match between images of the same object in different orientations. Elimination of these parameters may require more database images with closer angular spacing, depending on the particular embodiment.

7. Parallel processing can be utilized to increase computing power.

This technique is similar to that described by Betke & Makris in "Fast Object Recognition in Noisy Images Using Simulated Annealing", 1994, with the following important distinctions:

The current algorithm is robust with respect to occlusion. This is made possible by varying size and position of LIDs in database images, during the search process, in order to match non-occluded portions of database images.

The current algorithm can identify 3-dimensional objects by containing views of objects from many orientations in the database.

The current algorithm uses database clustering to enable rapid searching of large databases.

The current algorithm uses circular LIDs.

In addition to containing image information, the database 108 also contains address information. After the target object 100 has been identified, the database 108 is searched to find information corresponding to the target object 100. This information can be an information address, such as an Internet URL. The identification server 106 then sends this information, in the form of the target object information 109, to the terminal 102. Depending on the particular embodiment of the invention, the target object information 109 may include, but not be limited to, one or more of the following items of information pertaining to the target object 100:

Information address (e.g., Internet URL);
Identity (e.g., object name, number, classification, etc.);
Position;
Orientation;
Size;
Color;
Status;
Information decoded from and/or referenced by symbols (e.g. information coded in a barcode or a URL referenced by such a barcode); and Other data (e.g. alphanumerical text).

Thus, the identification server determines the identity and/or various attributes of the target object 100 from the image data 105.

The target object information 109 is sent to the terminal 102. This information usually flows via the same communication path used to send the image data 105 from the terminal 102 to the identification server 106, but this is not necessarily the case. This method of this flow information depends on the particular embodiment of the invention.

The terminal 102 receives the target object information 109. The terminal 102 then performs some action or actions based on the target object information 109. This action or actions may include, but not be limited to:

Accessing a web site.

Accessing or initiating a software process on the terminal 102.

Accessing or initiating a software process on another computer via a network or networks such as the Internet.

Accessing a web service (a software service accessed via the Internet).

Initiating a telephone call (if the terminal 102 includes such capability) to a telephone number that may be included in or determined by the target object Information, may be stored in the terminal 102, or may be entered by the user.

Initiating a radio communication (if the terminal 102 includes such capability) using a radio frequency that may be included in or determined by the target object Information, may be stored in the terminal 102, or may be entered by the user.

Sending information that is included in the target object information 109 to a web site, a software process (on another computer or on the terminal 102), or a hardware component.

Displaying information, via the screen or other visual indication, such as text, graphics, animations, video, or indicator lights.

Producing an audio signal or sound, including playing music.

In many embodiments, the terminal 102 sends the target object information 109 to the browser 110. The browser 110 may or may not exist in the terminal 102, depending on the particular embodiment of the invention. The browser 110 is a software component, hardware component, or both, that is capable of communicating with and accessing information from a computer at an information address contained in target object information 109.

In most embodiments the browser 110 will be a web browser, embedded in the terminal 102, capable of accessing and communicating with web sites via a network or networks such as the Internet. In some embodiments, however, such as those that only involve displaying the identity, position, orientation, or status of the target object 100, the browser 110 may be a software component or application that displays or provides the target object information 109 to a human user or to another software component or application.

In embodiments wherein the browser 110 is a web browser, the browser 110 connects to the content server 111 located at the information address (typically an Internet URL) included in the target object information 109. This connection is effected by the terminal 102 and the browser 110 acting in concert. The content server 111 is an information server and computing system. The connection and information exchanged between the terminal 102 and the content server 111 generally is accomplished via standard Internet and wireless network software, protocols (e.g. HTTP, WAP, etc.), and networks, although any information exchange technique can be used. The physical network connection depends on the system architecture of the particular embodiment but in most embodiments will involve a wireless network and the Internet. This physical network will most likely be the same network used to connect the terminal 102 and the identification server 106.

The content server 111 sends content information to the terminal 102 and browser 110. This content information usually is pertinent to the target object 100 and can be text, audio, video, graphics, or information in any form that is usable by the browser 110 and terminal 102. The terminal 102 and browser 110 send, in some embodiments, additional information to the content server 111. This additional information can be information such as the identity of the user of the terminal 102 or the location of the user of the terminal 102 (as determined from a GPS system or a radio-frequency ranging system). In some embodiments such information is provided to the content server by the wireless network carrier.

The user can perform ongoing interactions with the content server 111. For example, depending on the embodiment of the invention and the applications, the user can:

Listen to streaming audio samples if the target object 100 is an audio recording (e.g., compact audio disc).

Purchase the target object 100 via on-line transaction, with the purchase amount billed to an account linked to the terminal 102, to the individual user, to a bank account, or to a credit card.

In some embodiments the content server 111 may reside within the terminal 102. In such embodiments, the communication between the terminal 102 and the content server 111 does not occur via a network but rather occurs within the terminal 102.

In embodiments wherein the target object 100 includes or is a device capable of communicating with other devices or computers via a network or networks such as the Internet, and wherein the target object information 109 includes adequate identification (such as a sign, number, or barcode) of the specific target object 100, the content server 111 connects to and exchanges information with the target object 100 via a network or networks such as the Internet. In this type of embodiment, the terminal 102 is connected to the content server 111 and the content server 111 is connected to the target object 100. Thus, the terminal 102 and target object 100 can communicate via the content server 111. This enables the user to interact with the target object 100 despite the lack of a direct connection between the target object 100 and the terminal 102.

The following are examples of embodiments of the invention.

Figure 5:
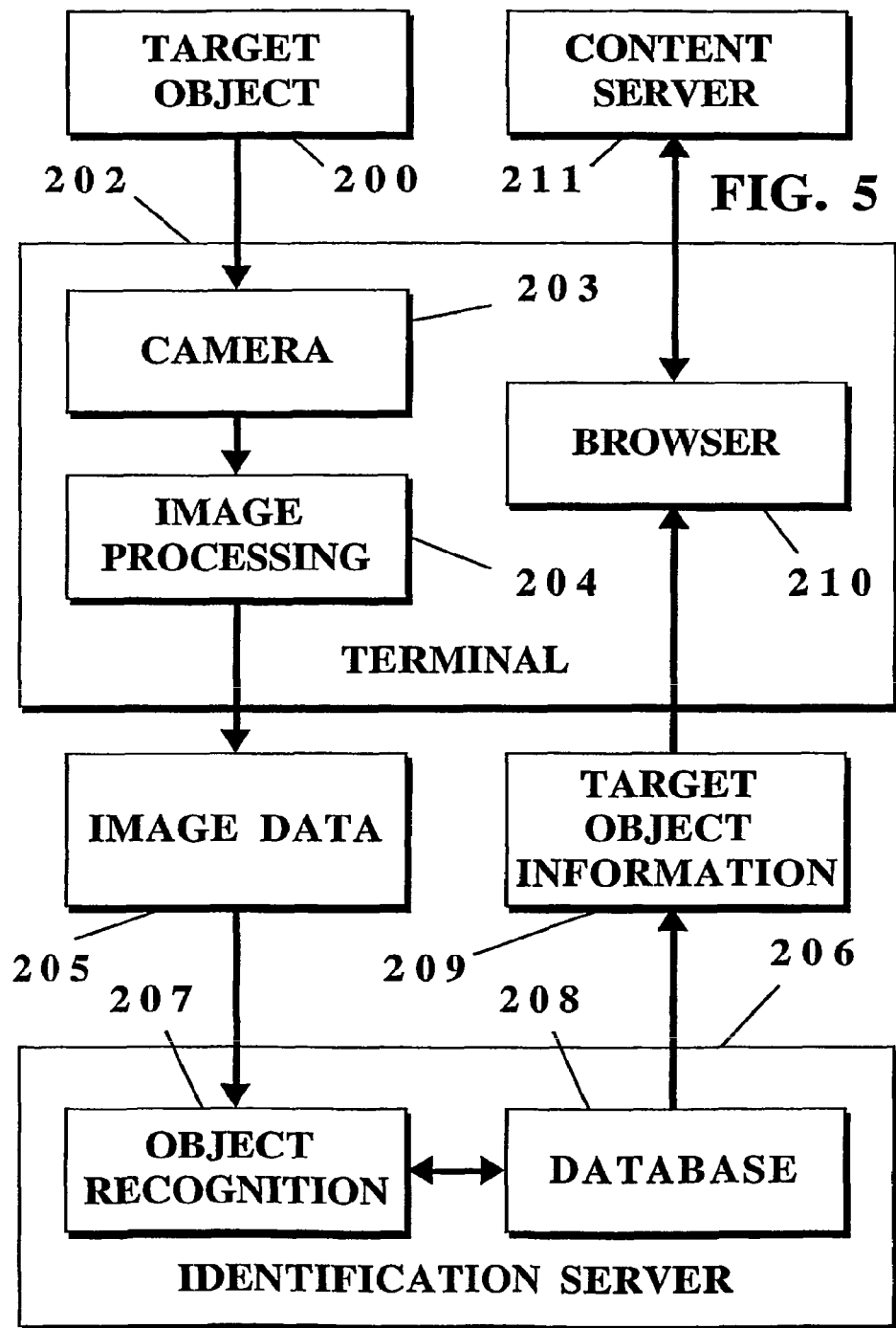
FIG. 5 is a schematic block diagram similar to FIG. 4 for cellular telephone and personal data assistant (PDA) applications.

FIG. 5 shows a preferred embodiment of the invention that uses a cellular telephone, PDA, or such mobile device equipped with computational capability, a digital camera, and a wireless network connection, as the terminal 202 corresponding to the terminal 102 in FIG. 4. In this embodiment, the terminal 202 communicates with the identification server 206 and the content server 211 via networks such as a cellular telephone network and the Internet.

This embodiment can be used for applications such as the following ("User" refers to the person operating the terminal 202, and the terminal 202 is a cellular telephone, PDA, or similar device, and "point and click" refers to the operation of the User capturing imagery of the target object 200 and initiating the transfer of the image data 205 to the identification server 206).

The User "points and clicks" the terminal 202 at a compact disc (CD) containing recorded music or a digital video disc (DVD) containing recorded video. The terminal 202 browser connects to the URL corresponding to the CD or DVD and displays a menu of options from which the user can select. From this menu, the user can listen to streaming audio samples of the CD or streaming video samples of the DVD, or can purchase the CD or DVD.

The User "points and clicks" the terminal 202 at a print media advertisement, poster, or billboard advertising a movie, music recording, video, or other entertainment. The browser 210 connects to the URL corresponding to the advertised item and the user can listen to streaming audio samples, purchase streaming video samples, obtain show times, or purchase the item or tickets.

The User "points and clicks" the terminal 202 at a television screen to interact with television programming in real-time. For example, the programming could consist of a product promotion involving a reduced price during a limited time. Users that "point and click" on this television programming during the promotion are linked to a web site at which they can purchase the product at the promotional price. Another example is a interactive television programming in which users "point and click" on the television screen at specific times, based on the on-screen content, to register votes, indicate actions, or connect to a web site through which they perform real time interactions with the on-screen program.

The User "points and clicks" on an object such as a consumer product, an advertisement for a product, a poster, etc., the terminal 202 makes a telephone call to the company selling the product, and the consumer has a direct discussion with a company representative regarding the company's product or service. In this case the company telephone number is included in the target object information 209. If the target object information 209 also includes the company URL then the User can interact with the company via both voice and Internet (via browser 210) simultaneously.

The User "points and clicks" on a vending machine (target object 200) that is equipped with a connection to a network such as the Internet and that has a unique identifying mark, such as a number. The terminal 202 connects to the content server 211 of the company that operates the vending machine. The identification server identifies the particular vending machine by identifying and decoding the unique identifying mark. The identity of the particular machine is included in the target object information 209 and is sent from the terminal 202 to the content server 211. The content server 211, having the identification of the particular vending machine (target object 200), initiates communication with the vending machine. The User performs a transaction with the vending machine, such as purchasing a product, using his terminal 202 that communicates with the vending machine via the content server 211.

The User "points and clicks" on part of a machine, such as an aircraft part. The terminal 202 then displays information pertinent to the part, such as maintenance instructions or repair history.

The User "points and clicks" on a magazine or newspaper article and link to streaming audio or video content, further information, etc.

The User "points and clicks" on an automobile. The location of the terminal 206 is determined by a Global Position System receiver in the terminal 206, by cellular network radio ranging, or by another technique. The position of the terminal 202 is sent to the content server 211. The content server provides the User with information regarding the automobile, such as price and features, and furthermore, based on the position information, provides the User with the location of a nearby automobile dealer that sells the car. This same technique can be used to direct Users to nearby retail stores selling items appearing in magazine advertisements that Users "point and click" on.

For visually impaired people:

Click on any item in a store and the device speaks the name of the item and price to you (the items must be in the database).

Click on a newspaper or magazine article and the device reads the article to you.

Click on a sign (building, streetsign, etc.) and the device reads the sign to you and provides any addition pertinent information (the signs must be in the database).

Figure 6:
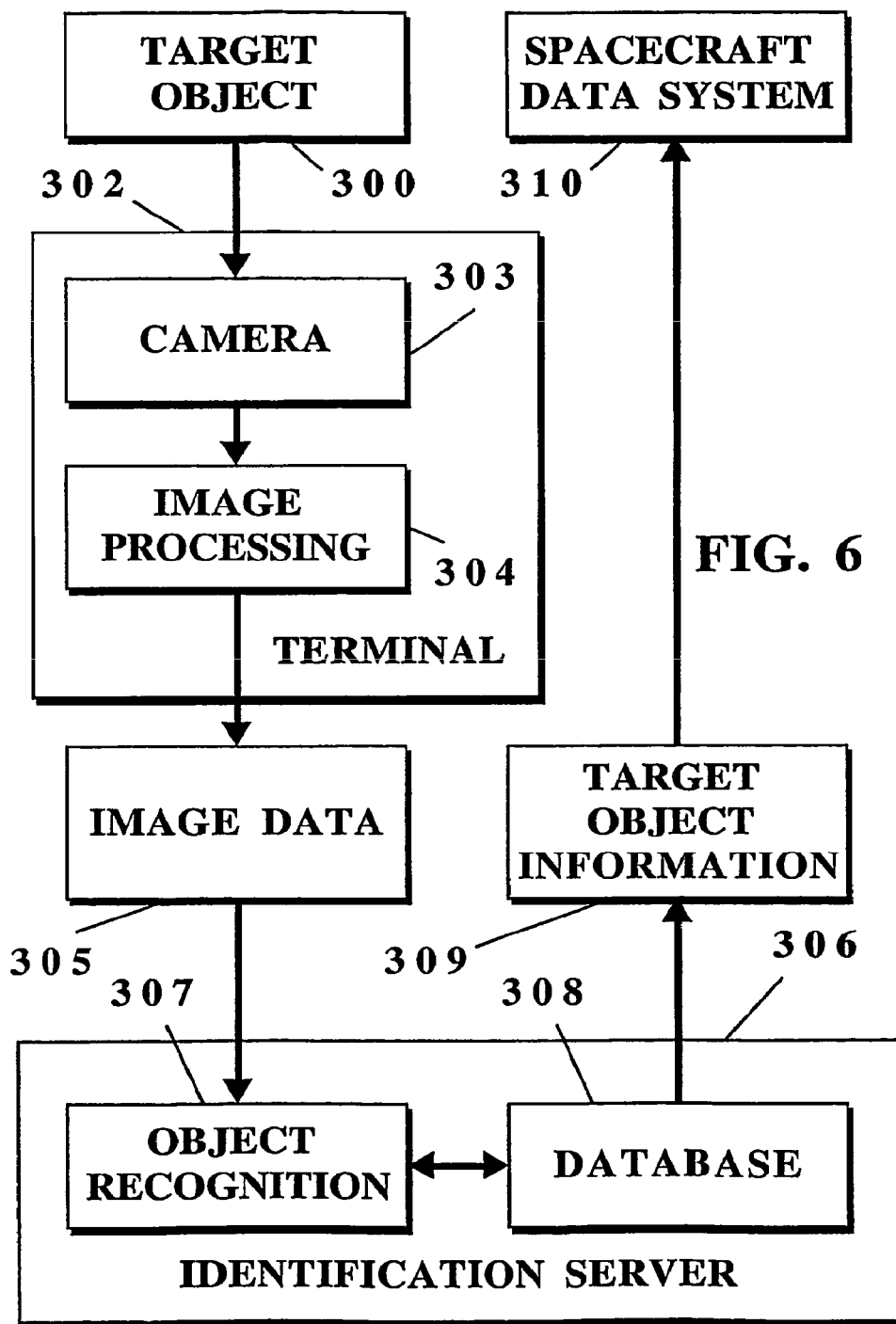
FIG. 6 is a schematic block diagram for spacecraft applications.

FIG. 6 shows an embodiment of the invention for spacecraft applications. In this embodiment, all components of the system (except the target object 300) are onboard a Spacecraft. The target object 300 is another spacecraft or object. This embodiment is used to determine the position and orientation of the target object 300 relative to the Spacecraft so that this information can be used in navigating, guiding, and maneuvering the spacecraft relative to the target object 300. An example use of this embodiment would be in autonomous spacecraft rendezvous and docking.

This embodiment determines the position and orientation of the target object 300, relative to the Spacecraft, as determined by the position, orientation, and size of the target object 300 in the imagery captured by the camera 303, by comparing the imagery with views of the target object 300 from different orientations that are stored in the database 308. The relative position and orientation of the target object 300 are output in the target object information, so that the spacecraft data system 310 can use this information in planning trajectories and maneuvers.

INDUSTRIAL APPLICABILITY

The industrial applicability is anywhere that objects are to be identified by a digital optical representation of the object.

What is claimed is:

1. A method of interacting with an environment, the method comprising:
    capturing, via a mobile device, a video stream representing a physical environment;
    analyzing, via an image processing platform, the video stream to determine whether the video stream includes at least one identifying mark associated with at least one object within the physical environment;
    recognizing the at least one identifying mark according to its type as being associated with an address associated with the physical environment and content information; and
    displaying, via the address, the content information to a user.

2. The method of claim 1, wherein the mobile device comprises a camera configured to capture at least one of the video stream, image data, and a still image.

3. The method of claim 1, wherein the video stream comprises a real-time video stream.

4. The method of claim 1, wherein the at least one identifying mark is associated with one object in the physical environment.

5. The method of claim 1, wherein the at least one object is associated with a human.

6. The method of claim 5, wherein the at least one object comprises a human face.

7. The method of claim 1, further comprising identifying the at least one object as a target object.

8. The method of claim 7, further comprising obtaining the address at least in part based on target object information associated with the target object.

9. The method of claim 7, wherein the target object represents at least one of the following: a building, a store, a vehicle, a media box, a person, a passport, a driver's license, a poster, an advertisement, on-screen content, a product, a beverage, a sign, a newspaper, a magazine, a radio frequency, and a machine part.

10. The method of claim 1, wherein the at least one identifying mark comprises at least one of the following: alphanumeric characters, a barcode, a matrix code, a symbol, a feature, and a frequency.

11. The method of claim 1, further comprising obtaining additional information associated with the physical environment.

12. The method of claim 11, wherein the additional information includes at least one of the following: a location and a time.

13. The method of claim 1, wherein displaying the content information includes displaying interactive video content.

14. The method of claim 1, further comprising allowing an interaction with the content information.

15. The method of claim 1, wherein displaying the content information includes displaying interactive product information.

16. The method of claim 1, further comprising allowing initiation of a purchase of a product based on the content information.

17. The method of claim 1, further comprising enabling a payment transaction based on the content information.

18. The method of claim 1, further comprising enabling an on-line transaction associated with a purchase amount based on the content information.

19. A mobile device comprising:
a sensor configured to capture video stream representing a physical environment; and
an image processing platform configured to:
analyze, via an image processing platform, the video stream to determine whether the video stream includes at least one identifying mark associated with at least one object within the physical environment;
recognize the at least one identifying mark according to its type as being associated with an address associated with the physical environment and content information; and
display, via the address, the content information to a user.

20. The mobile device of claim 19, wherein the sensor comprises a camera configured to capture at least one of the video stream, image data, and a still image.

21. The mobile device of claim 19, wherein the video stream comprises a real-time video stream.

22. The mobile device of claim 19, wherein the at least one identifying mark is associated with one object in the physical environment.

23. The mobile device of claim 19, wherein the at least one object is associated with a human.

24. The mobile device of claim 23, wherein the at least one object comprises a human face.

25. The mobile device of claim 19, wherein the image processing platform is further configured to identify the at least one object as a target object.

26. The mobile device of claim 25, wherein the image processing platform is further configured to obtain the content information at least in part based on target object information associated with the target object.

27. The mobile device of claim 25, wherein the target object represents at least one of the following: a building, a store, a vehicle, a media box, a person, a passport, a driver's license, a poster, an advertisement, on-screen content, a product, a beverage, a sign, a newspaper, a magazine, a radio frequency, and a machine part.

28. The mobile device of claim 19, wherein the at least one identifying mark comprises at least one of the following: alphanumeric characters, a barcode, a matrix code, a symbol, a feature, and a frequency.

29. The mobile device of claim 19, wherein the image processing platform is further configured to obtain additional information associated with the physical environment.

30. The mobile device of claim 29, wherein the additional information includes at least one of the following: a location and a time.

31. The mobile device of claim 19, wherein the image processing platform is further configured to display the content information as interactive video content.

32. The mobile device of claim 19, further comprising a display allowing interaction with content information.

33. The mobile device of claim 19, wherein the content information includes interactive product information.

34. The mobile device of claim 19, where in the content information enables an initiation of a purchase of a product.

35. The mobile device of claim 19, where in the content information enables an initiation of a payment transaction.

36. The mobile device of claim 19, where in the content information enables an initiation of an on-line transaction associated with a purchase amount based on the content information.

37. A computer program product comprising non-transitory computer readable medium storing instructions that cause a processor to execute the steps of:
capturing, via a mobile device, a video stream representing a physical environment;
analyzing, via an image processing platform, the video stream to determine whether the video stream includes at least one identifying mark associated with at least one object within the physical environment;
identifying the at least one identifying mark according to its type as being associated with an address associated with the physical environment and content information; and
displaying, via the address, the content information to a user.

38. The computer program product of claim 37, wherein the mobile device comprises a camera configured to capture at least one of the video stream, image data, and a still image.

39. The computer program product of claim 37, wherein the video stream comprises a real-time video stream.

40. The computer program product of claim 37, wherein the at least one identifying mark is associated with one object in the physical environment.

41. The computer program product of claim 37, wherein the at least one object is associated with a human.

42. The computer program product of claim 41, wherein the at least one object comprises a human face.

43. The computer program product of claim 37, wherein the instructions further cause the processor to execute the step of identifying the at least one object as a target object.

44. The computer program product of claim 43, wherein the instructions further cause the processor to execute the step of obtaining the address at least in part based on target object information associated with the target object.

45. The computer program product of claim 43, wherein the target object represents at least one of the following: a building, a store, a vehicle, a media box, a person, a passport, a driver's license, a poster, an advertisement, on-screen content, a product, a beverage, a sign, a newspaper, a magazine, a radio frequency, and a machine part.

46. The computer program product of claim 37, wherein the at least one identifying mark comprises at least one of the following: alphanumeric characters, a barcode, a matrix code, a symbol, a feature, and a frequency.

47. The computer program product of claim 37, wherein the instructions further cause the processor to execute the step of obtaining additional information associated with the physical environment.

48. The computer program product of claim 47, wherein the additional information includes at least one of the following: a location and a time.

49. The method of claim 37, wherein displaying the content information includes the step of displaying interactive video content.

50. The computer program product of claim 37, wherein the instructions further cause the processor to execute the step of allowing an interaction with the content information.

51. The computer program product of claim 37, wherein the step of displaying the content information includes displaying interactive product information.

52. The computer program product of claim 37, wherein the instructions further cause the processor to execute the step of allowing an initiation of a purchase of a product based on the content information.

53. The computer program product of claim 37, wherein the instructions further cause the processor to execute the step of enabling an initiation of a payment transaction based on the content information.

54. The computer program product of claim 37, wherein the instructions further cause the processor to execute the step of conducting an on-line transaction associated with a purchase amount based on the content information.

* * * * *